United States Patent [19]

Baldwin et al.

[11] 4,311,586

[45] Jan. 19, 1982

[54] SOLVENT MIXING IN HPLC USING LOW PRESSURE SOLVENT METERING PUMPS

[75] Inventors: Lawrence G. Baldwin, Smithville; Burney J. Ehrlich, Austin; Jack B. Dixon, Georgetown, all of Tex.

[73] Assignee: Tracor, Inc., Austin, Tex.

[21] Appl. No.: 142,679

[22] Filed: Apr. 22, 1980

[51] Int. Cl.$^3$ .............................................. B01D 15/08
[52] U.S. Cl. .............................. 210/101; 210/198.2; 73/61.1 C
[58] Field of Search .................... 210/96.1, 101, 198.2; 73/61.1 C

[56] References Cited

U.S. PATENT DOCUMENTS

| | | | |
|---|---|---|---|
| 3,398,079 | 8/1968 | Arthur | 204/195 |
| 3,398,689 | 8/1968 | Allington | 210/101 X |
| 3,917,531 | 11/1975 | Magnussen | 210/101 |
| 3,985,019 | 10/1976 | Boehme | 73/61.1 C |
| 3,997,298 | 12/1976 | McLafferty | 210/198.2 |
| 4,018,685 | 4/1977 | Saunders | 210/198.2 |
| 4,063,077 | 12/1977 | Wright | 210/198.2 |
| 4,128,476 | 12/1978 | Rock | 210/101 |

OTHER PUBLICATIONS

Liquid Chromatography by Tracor Inc., Austin, Texas.
Gradient Elution Facilities for LC Using the Continuous and Incremental Methods of Solvent Mixing, by Scott, Journal of Chromatography Science, vol. 9, Jul. 1971, pp. 385–389.
A Multifunctional Gradient Device for Use in High Speed Liquid Chromatography by Byrne et al, in the Journal of Chromatography Science, vol. 9, Oct. 1971, pp. 592–595.
Accuracy and Reproducibility in a Twp-Pump Gradient HPLC by Savage, International Laboratory, May/-Jun. 1979, pp. 191–199.
Theoretical Study of the Gradient Elution Profiles Obtained with Syringe-Type Pumps in Liquid Chromatography by Martin et al, Journal of Chromatography, 151, (1978) 267–289.

Primary Examiner—John Adee
Attorney, Agent, or Firm—Arnold, White & Durkee

[57] ABSTRACT

A liquid chromatograph for HPLC utilizes low pressure solvent metering pumps for solvent mixing in series with a high pressure pump driving the column. Solvent mixture is provided at a flow based upon the intake demand of the high pressure pump. Such operation is obtained by the use of flow control apparatus disposed between the solvent metering pumps and the high pressure pump. The flow control apparatus includes a detector cell disposed in the solvent mixture flow path between the metering pumps and the high pressure pump. The cell has an inlet port for receiving an input flow of solvent mixture into the cell from the solvent mixing means, an outlet port for withdrawal of an output flow of solvent mixture by the high pressure pumps, and a reservoir between the inlet and outlet ports for holding a volume of solvent mixture accumulated in an amount dependent upon the relative flow rates of the cell input and output flow. The cell having first and second spaced-apart electrodes in contact with the solvent mixture accumulated in the cell. One of the electrodes receives an applied electrical excitation. The other electrode senses the applied excitation through the accumulated solvent mixture and produces an excitation response functionally related to the volume of accumulated solvent mixture. An electrical control circuit connected to the detector cell and coupled to the pump speed controller responds to the detector excitation response and produces a control input to the pump controller that selectively inhibits and enables operation of the solvent metering pumps as required to meet the intake of the high pressure pump without wastage or excessive loss of compositional response.

5 Claims, 13 Drawing Figures

SOLVENT MIXING IN HPLC USING LOW PRESSURE SOLVENT METERING PUMPS

BACKGROUND OF THE INVENTION

The present invention relates to liquid chromatographic systems; and more particularly, it relates to solvent mixing in high performance liquid chromatography (HPLC).

Liquid chromatography is an analytical method used to isolate and identify the components of a mixture. Liquid chromatography involves a separation of the components of a mixture in solution by selective adsorption and differences in the rates at which the individual components of the mixture migrate through a stationary medium under the influence of a mobile phase.

In liquid adsorption chromatography, the stationary phase consists of a tubular column packed with an adsorbent material. The mobile phase for carrying an analysis sample through the column, commonly referred to as the "carrier," is a solvent mixture comprising two or more miscible liquids, which is introduced into the column. An equilibrium is established for the individual components of a sample mixture according to the "attraction" of each to the stationary phase and according to the solubility of each in the carrier solvent mixture. The rate at which a solute passes through the column of the chromatograph is dependent upon the equilibria existing, and separations occur where the distributions differ.

All liquid chromatography systems include a moving solvent; a means of producing solvent motion, such as gravity or (in more recently developed equipment) a pump; a means of sample introduction; a fractionating column; and a detector.

Operation of a liquid chromatography system with a carrier of two or more solvents mixed in constant, non-varying proportions is referred to as "isocratic" operation. Sometimes, however, it is desirable to operate the liquid chromatographic system using a carrier in which the ratios of the liquids in the solvent mixture vary over time in accordance with some predetermined gradient. This type of operation is referred to as "gradient elution," and the gradient profiles referred to as solvent programs. Within the category of gradient elution operation, the ratios in the solvent mixture can be made to increase at a fixed rate, i.e., linear gradient, or at an increasing rate of change, i.e., convex gradient, or at a decreasing rate of change, i.e., concave gradient, by appropriate control of the solvent mixing apparatus.

Solvent mixing apparatus to provide the carrier has been accomplished using a multiple, parallel pump arrangement in which each pump meters a different solvent into a common outlet flow line to form a solvent mixture. The total flow rate of the solvent mixture approximately equals the sum of the individual solvent flow rates with the composition of the solvent mixture being determined by the ratios of the flow rates of the individual solvents. Gradient compositions are obtained by control of the pumps to vary the relative flow rates of the pumps during a chromatograph analysis run. Apparatus operating in this manner to form a two-component solvent mixture at a constant rate of flow for introduction into the column of a liquid chromatograph, and providing gradient elution operation, is disclosed in U.S. Pat. No. 3,398,689 issued to R. W. Allington on Aug. 27, 1968. The Model 332 dual-pump gradient liquid chromatograph system of Altex Scientific, Inc., described by M. Savage in "Accuracy and reproducibility in a two-pump gradient HPLC," *International Lab.*, May/June, 1979, pp. 190–199 (1979), also exemplifies metering pump solvent mixing apparatus.

It is conventional in prior art metering pump solvent mixing apparatus to utilize high pressure reciprocating pumps to meter solvents into a common high pressure flow line that feeds solvent mixture directly to the chromatograph column. Such is the teaching of the 3,398,689 patent to Allington. M. Savage diagrams and describes a solvent mixing apparatus having two high pressure pumps metering solvents into a high pressure, dynamic stirring mixing chamber from which the column is directly driven. By "high pressure," reference is thereby being made to a pressure level above ambient or atmospheric pressure which is sufficient to drive a chromatograph column.

At high pressure, accurate solvent mixing is difficult to obtain. For one, reciprocating pumps, which are typically used, produce pressure pulsing upon piston direction reversal when check valve closure occurs. This causes transient flow rate variations that produce mixing errors. Also, accurate speed control of high pressure pumps is difficult to obtain. Particular difficulty is encountered in driving a high pressure pump at low speed, as would be required to obtain a low flow rate in a small percentage solvent mixture. Furthermore, undesired solvent compressibility effects are most pronounced at high pressure. "Compressibility effects" refers to changes in the flow rate of a solvent through a metering pump as back pressure changes during pumping of the solvent. Solvent metering pumps commonly are compensated by a solvent compressibility correction factor based on measured pressure. However, the correction factor does not hold true for all solvents because of varying characteristics (compressibility and viscosity). In HPLC, solvents of widely varying characteristics are encountered. Therefore, as a solvent mixture is being formed, the compressibility effects will produce compositional accuracy errors.

As can readily be appreciated now, use of reciprocating metering pumps at low pressure can enhance accuracy in solvent mixing. The enhancement is most pronounced if solvent mixing is done at essentially ambient or atmospheric pressure.

The use of low pressure metering pumps, however, requires a high pressure pump, referred to as an HPLC pump, in series to drive the chromatograph column. Unless the total flow rate of solvent mixture from the metering pumps is matched with the intake flow rate of the HPLC pump, the composition of the solvent mixture reaching the column may be affected. It is, of course, apparent that if the HPLC pump has a greater flow rate than the total flow rate from the metering pumps, the HPLC pump will develop a vapor lock condition and there will be a total loss of flow to the chromatograph column. But also, if the HPLC pump produces a lesser flow rate than the total flow from the metering pumps, the metering pumps will be operating against the back pressure of the HPLC pump which will affect the individual metering pump flow rates in an unknown manner. Alterations in the metering pump flow rates will, of course, alter the solvent mixture composition, such that the constituents of the solvent mixture introduced to the chromatograph column will be of unknown proportions.

One possible solution to the problem of unequal flow rates would be inclusion of a large volume surge tank. That is, a tank containing enough volume of solvent mixture to accommodate during a chromatograph run surges in either the total flow rate of the metering pumps or in the intake flow rate of the HPLC pump. Although the inclusion of a surge tank would obviate much of the operational difficulty resulting from differences in the flow rates, the surge tank would add substantially to the total volume between the point where the solvents come together and the chromatograph column inlet.

In an effort to obviate the problems attendant high pressure metering pump solvent mixing apparatus, several systems have been developed in which solvent mixing is accomplished by use of a proportioning valve mechanism on the low pressure intake side of a high pressure chromatograph system pump driving the column. Among the first to disclose such solvent mixing apparatus was S. H. Byrne et al, "A Multifunctional Gradient Device for Use in High Speed L.C.," 9 *J. Chrom. Sci.* 592 (1971). Other disclosures and discussions of such apparatus are found in *Modern Practice of Liquid Chromatography*, J. Wiley & Sons, Interscience (1976) authored by J. J. Kirkland; *Contemporary Liquid Chromatography*, J. Wiley & Sons, Interscience (1976) authored by R. P. W. Scott; and 3 *Instrumentation for HPLC*, pp. 41-62, Elsevier Sci. Pub. Co., Amsterdam (1978) authored by J. F. K. Huber. A single, two-way proportioning valve system is also disclosed in U.S. Pat. No. 4,018,685 issued to Saunders et al on Apr. 19, 1977.

In solvent mixing using a proportioning valve, discrete slugs or pulses of solvent are drawn at low pressure into a mixing chamber. This may be accomplished by gravity flow or by a single low pressure pump. In order to drive the column, a high pressure system pump is required between the mixing chamber and the column. Since a constant flow rate to the column is essential, the system pump typically is one of a design which intakes solvent mixture in gulps and builds a liquid head to discharge. If the intake gulps of the system pump should become synchronized with actuations of the proportioning valve to access one of the solvents, discrete slugs of pure solvent are alternately placed into the flow to the column causing fluctuations in the composition. Because of the lengthy minimum response times for a proportioning valve, cycle time must by necessity be several seconds in duration, so merely speeding up the repetition of valve cycling is not an available solution.

A technique for minimizing the solvent slug mixing problem involving the use of a breather reservoir between the mixer and the chromatograph system pump is embodied in the Tracor Model 980 Liquid Chromatograph. In this technique, solvent mixture is provided to the breather reservoir at a flow rate greater than the intake flow rate of the system pump. The reservoir has an overflow vent to waste. However, because of the expense of some solvents, such technique is not favored in some instances.

Thus, although the advantages of using low pressure solvent mixing in an HPLC are apparent, it has not heretofore been realized in practice with these types of solvent mixing apparatus without substantial sacrifice because of the undesired results of interfacing low pressure solvent mixing apparatus to the required high pressure chromatograph system pump.

As additional information with regard to liquid chromatograph systems having solvent mixing apparatus, it is pointed out that, particularly for systems capable of gradient elution operation, a controller is conventionally included within the system for establishing the composition of the solvent mixture produced and the total flow rate at which it is being provided.

In solvent mixing apparatus comprising solvent metering pumps, each of which provides a flow of one solvent at a rate dependent upon its speed of operation, with the combined flows of the pumps forming a solvent mixture at a total flow rate that is approximately the sum of the individual solvent flow rates, the controller acts to control the speed of the pumps. In the apparatus disclosed in the 3,398,689 patent to Allington, solvent metering pump control is provided by a controller mechanism producing an electrical control signal that is applied to motor control circuits which regulate the power to motors driving the solvent metering pumps. The controller mechanism comprises a potentiometer mechanically operated by linkage connected to a cam cut in a way related to the desired solvent composition with respect to time. Alternatively, accurate speed control of the solvent metering pumps may be provided by a microprocessor-based controller, as exemplified by the Model 332 dual-pump gradient liquid chromatograph system of Altex Scientific, Inc. A dual-pump gradient system using pulse-width modulated signals obtained from a microprocessor to control the operation of stepping motor driven solvent metering pumps is described by M. Savage in "Accuracy and reproducibility in a two-pump gradient HPLC," *International Lab.*, May/June, 1979, pp. 190-199 (1979).

In solvent mixing apparatus comprising a proportioning valve accessing each of a plurality of solvent sources for a predetermined portion of a cycle of operation for time share mixing, with a pump delivering accessed solvents into a mixer from solvent mixture is provided, the rate at which the solvent mixture is provided is dependent upon the speed of the pump. Accordingly, the controller acts to establish solvent mixture composition by controlling the time duration that each solvent is accessed within a cycle of valve operation, and acts to establish the rate at which solvent mixture is being provided by controlling the speed of the solvent delivery pump. Representative controllers for operating proportioning valve-type solvent mixing apparatus are found in U.S. Pat. Nos. 4,063,077 and 4,128,476.

SUMMARY OF THE INVENTION

The present invention provides improvements in liquid chromatography systems in which two or more solvents are mixed in prescribed proportions to form a solvent mixture ultimately to be introduced into a chromatograph column as a carrier for the mobile phase.

In particular, the present invention has utility and provides an improvement in a liquid chromatograph having solvent mixing apparatus which includes two or more solvent metering pumps, each providing a flow of one solvent at a rate dependent upon pump speed, with the individual solvent flows being combined to form a solvent mixture of a composition determined by the relative flow rates of the individual solvent flows and at a total flow rate that is the sum of the individual flow rates. Control of the speeds of the metering pumps and regulation of the total flow rate of the solvent mixture is provided by a pump speed controller.

Aspects of the present invention may, however, also provide for improvement of a liquid chormatograph having solvent mixing apparatus in the form of a proportioning valve mechanism which accesses individual solvents on a time share basis for withdrawal and delivery to a mixing chamber, such as by a low pressure pump. The volume of each individual solvent withdrawn during the time it is accessed (and thus the volume of solvent mixture formed within each cycle of operation of the proportioning valve mechanism) is established by the speed of the pump as it withdraws the solvents. The formation of a certain volume of solvent mixture within each cycle of operation of the proportioning valve mechanism and made available from the mixing chamber constitutes a flow of solvent mixture at a particular flow rate.

Recognizing the need for enhanced compositional accuracy in solvent mixtures introduced to the column of a liquid chromatograph, a feature of the present invention is that of providing for the first time realization of low pressure solvent mixing in a liquid chromatograph without sacrifice of compositional response or substantial solvent wastage.

An additional feature of the present invention is that of controlling the rate at which solvent mixture is being provided from solvent mixing apparatus in response to the supply demand of a high pressure pump driving the chromatographic column.

Therefore, the present invention can be summarized in one aspect as an improvement in a liquid chromatograph comprising in combination low pressure solvent metering pumps in the solvent mixing apparatus, a high pressure pump driving the column, and flow control apparatus disposed between the metering pumps and the high pressure pump sensing the supply demand of the high pressure pump relative to the total flow rate at which solvent mixture is being provided and producing a control input to the controller to effect an increase or decrease in solvent mixture production.

In accordance with another aspect of the present invention, a sensing detector cell is disposed in the solvent mixture flow path between the solvent mixing apparatus and a chromatograph system pump provided to drive the column. The detector is sensitive to the relative flow rates at which solvent mixture is being provided by the solvent mixing apparatus and taken in by the chromatograph system pump, and produces an output signal indicative of the relative flow rates. An electrical control circuit coupled to the pump speed controller to provide a control input thereto receives the sensing detector cell output signal and in response controls the rate at which solvent mixture is provided.

Further in accordance with the present invention, the sensing detector cell has an inlet port for receiving a supply flow of solvent mixture into the cell from the solvent mixing apparatus and an outlet port for withdrawal of an output flow of solvent mixture by the chromatograph system pump. A reservoir exists within the cell between the inlet and outlet ports to hold a volume of solvent mixture accumulating therein in an amount depending upon the relative flow rates of the cell supply flow and the cell output flow.

The relative rate at which solvent mixture is received and withdrawn is sensed by detecting the accumulated volume amount of solvent mixture in the cell, with the detector providing an output signal functionally related in one of its characteristics to the volume of the accumulated solvent mixture. In response to a sensing detector cell output signal, the electrical control circuit receiving the signal evaluates the volume amount of solvent mixture accumulated in the cell with respect to a preset reference volume amount.

The electrical control circuit by its control input to the pump speed controller effects a reduction in the total flow rate of the produced solvent mixture when the volume of solvent mixture accumulated in the cell exceeds the preset reference amount, and effects an increase in the total flow rate of the produced solvent mixture when the accumulated volume in the cell becomes less than the preset reference volume. Suitably, the electrical control circuit may inhibit operation of the solvent mixing apparatus altogether when the accumulated volume of solvent mixture in the cell exceeds the preset volume amount and enable the solvent mixing apparatus for operation when the volume amount of accumulated solvent mixture in the cell becomes less than the preset reference volume amount.

Preferably, and in accordance with another aspect of the present invention, detection of the volume amount of accumulated solvent mixture in the detector cell is made using an electrical measurement device sensitive to the volume amount of solvent mixture accumulated in the cell by reason of a change in a measured electrical property of the mixture with a change in volume. The measurement device provides an output signal representative of the volume amount of the accumulated solvent mixture in one of its parameters. In using an electrical measurement detection, the sensing detector cell includes first and second spaced-apart electrodes in contact with the solvent mixture accumulated in the cell, one of the electrodes being provided to receive an applied electrical excitation and the other electrode being provided to sense the applied excitation through the accumulated solvent mixture between the electrodes and produce an excitation response functionally related to the volume amount of the accumulated solvent mixture.

An electrical admittance measurement device has been discovered to be particularly suited for detecting the volume of a solvent mixture in the detector cell, which mixture may be composed of any of a variety of solvents which variously exhibit high conductivity to high dielectric characteristics.

Thus, the present invention provides improved compositional accuracy of solvent mixtures in an HPLC by dynamic control of the flow rate at which solvent mixing apparatus provides a solvent mixture. Dynamic flow control in accordance with the more narrow aspects of the present invention involves the use of an electrical admittance detecting cell in the flow path between solvent mixing apparatus operating to mix solvents at low pressure and a chromatograph system pump provided to drive the column. The cell comprises a cylindrical chamber of electrically conductive material having an inlet supply port through the sidewall defined by a tube for receiving an input flow of solvent mixture provided by the solvent mixing apparatus. A tube fitting in the bottom of the cell chamber defines an outlet port for withdrawal of solvent mixture from the cell by the chromatograph system pump at an output flow rate established by the intake flow rate of the system pump. The cell chamber provides a reservoir between the inlet and outlet ports in which solvent mixture may be accumulated. The volume amount of solvent mixture accumulated will depend upon the relative flow rates of the input and output flows of solvent mixture.

A rod of electrically conductive material is mounted concentrically in the center of the cell chamber and is insulated therefrom. Both the chamber and the rod act as electrodes, with an a.c. electrical excitation being applied to the cell chamber electrode and the rod electrode sensing the excitation through the resistance and dielectric effects of the solvent mixture material. The sensing electrode develops an electrical response signal in accordance with the electrical admittance properties of the solvent mixture material. The peak amplitude of the a.c. response signal varies in a proportion to the volume amount of solvent mixture accumulated in the cell chamber. Applying a squarewave signal as the cell excitation the cell response signal will be a series of pulses or spikes at the squarewave signal frequency, the exact waveform shape of the response signal being dependent upon the electrical characteristics of the solvent mixture material and the peak rise of the response signal being dependent upon the volume of the solvent material.

The sensing electrode is coupled to an electrical control circuit in which the admittance response signal is amplified and peak detected to develop a d.c. voltage level indicative of the solvent mixture volume accumulated in the cell. The output of the peak detector is applied to a comparator device for comparison with a reference voltage to provide a determination of the volume amount of accumulated solvent mixture relative to a reference volume amount. The comparator output is applied to a switching device coupled to the input of the metering pump drive circuits by an optical coupler device. When the volume of solvent mixture accumulated in the cell chamber exceeds the reference volume, the input to the metering pump drive circuits is grounded out; and when the volume is less than the reference volume, the input is released.

BRIEF DESCRIPTION OF THE DRAWINGS

A written description setting forth the best mode presently known for carrying out the present invention, and of the manner of implementing and using it, is provided by the following detailed description of an illustrative embodiment represented in the attached drawings wherein.

DETAILED DESCRIPTION OF AN ILLUSTRATIVE EMBODIMENT

Figure 1:
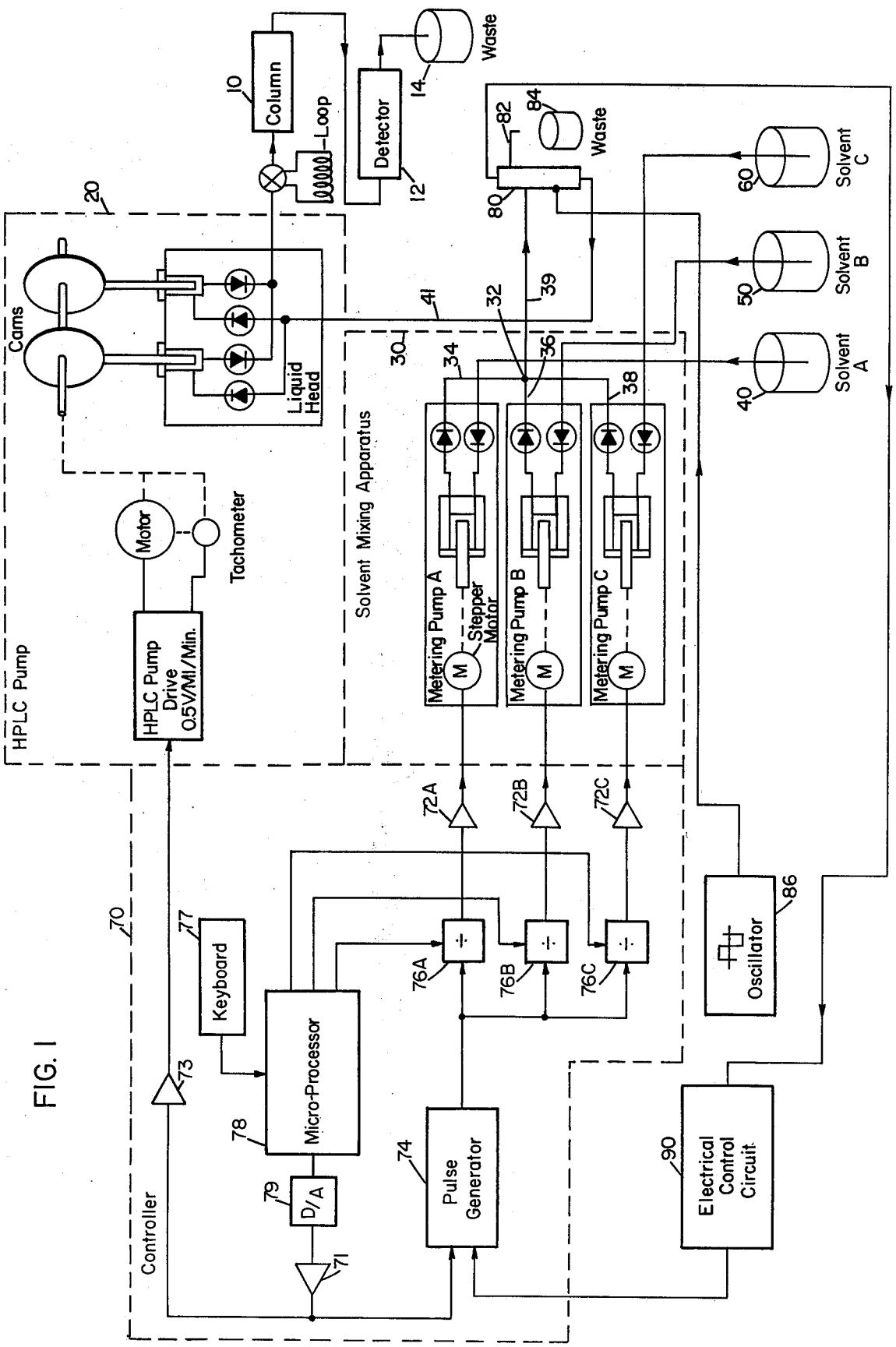
FIG. 1 is a functional diagram of a liquid chromatograph for HPLC improved in accordance with the present invention.

Referring to FIG. 1 of the drawings, there is functionally diagrammed a liquid chromatograph system improved in accordance with the present invention. The chromatograph system includes a column 10 for receiving a constant rate flow of solvent mixture. The output of column 10 is delivered to detector 12, with liquid passing through detector 12 being released to waste receptacle 14. Column 10 is supplied with a solvent mixture and driven by HPLC pump 20. The liquid chromatograph diagrammed is suitable for providing a solvent mixture by inclusion of solvent mixing apparatus 30 capable of mixing the three different solvents which are available. The three solvents are designated A, B and C; and are available from containers 40, 50 and 60, respectively. The composition and total flow rate of solvent mixture provided by solvent mixing apparatus 30 are established by controller 70.

A detector cell 80 is disposed in the solvent mixture flow path between solvent mixing apparatus 30 and HPLC pump 20. Detector cell 80 produces an output signal indicative of the relative flow rates at which solvent mixture is being provided by solvent mixing apparatus 30 and being demanded by HPLC pump 20. The detector cell output indication is applied to electrical control circuit 90 which produces a control input to controller 70 effective to cause controller 70 to change the total flow rate at which solvent mixture is being provided from solvent mixing apparatus 30 so as to supply the demands of HPLC pump 20.

HPLC pump 20 is a high pressure reciprocating pump. Preferably, HPLC pump 20 is a Tracor Model 950 or Model 951 high pressure pump. This pump has dual pistons actuated by a camshaft having separate cams for each piston. The camshaft is driven by an electric motor mechanically coupled thereto. An electrical HPLC pump drive circuit regulates the speed of the camshaft drive motor at a speed established in accordance with an electrical control input from controller 70. A tachometer mechanically coupled to the camshaft and the motor provides motor speed regulation feedback to the pump drive.

Figure 2:
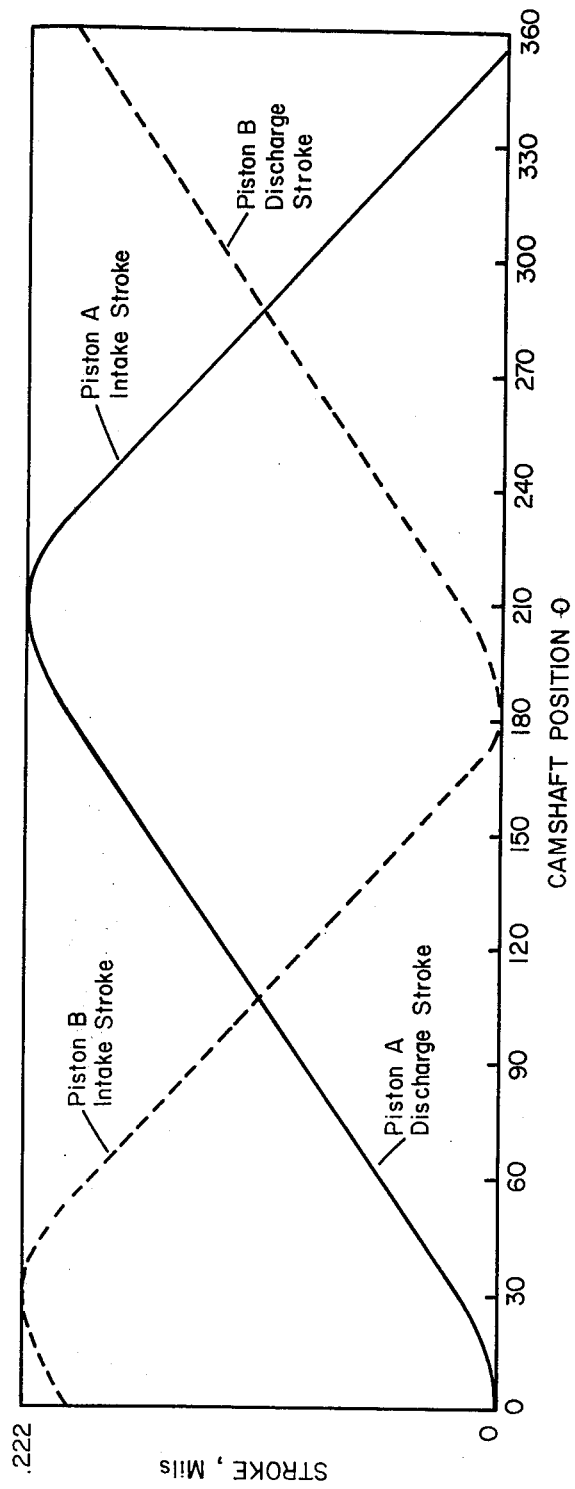
FIG. 2 is a diagram of the cam profile for the HPLC pump indicated in FIG. 1.

Referring briefly to FIG. 2, there is presented a diagram of the stroke of the HPLC pump pistons as a function of camshaft position. This diagram describes the profiles of the piston actuating cams. As indicated, the cams are cut to drive the pistons 180° out of phase with one another, but pump intake is for only 150°.

Figure 3A:
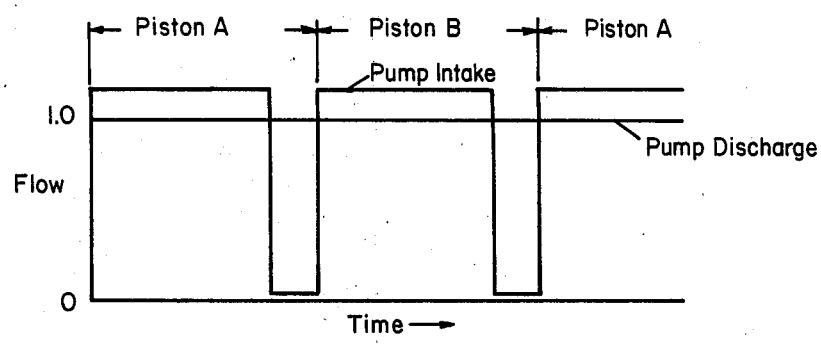
FIGS. 3A and 3B are diagrams of pump intake and discharge flow and column pressure for the HPLC pump indicated in FIG. 1.
Figure 3B:
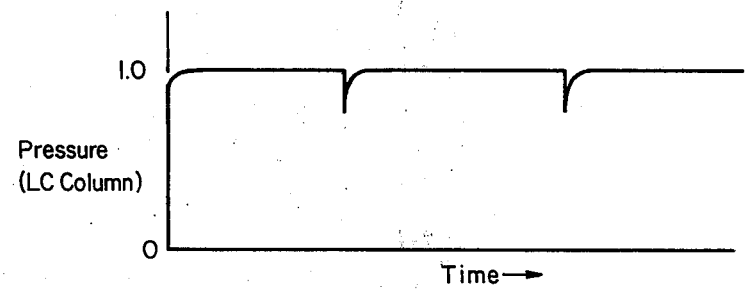

Referring to FIGS. 3A and 3B, the HPLC reciprocating pump characteristics are further indicated by the flow and pressure diagrams presented therein. In FIG. 3A, there is presented a comparison of HPLC reciprocating pump intake and idealized discharge flow. As shown, the dual pump pistons alternate taking in solvent mixture, with the pump taking in liquid in a discrete quantity during each piston intake stroke. The flow to the pump during each piston intake stroke is constant.

However, there is a "dead spot" in HPLC pump intake flow between the completion of the intake stroke of one piston and the beginning of the intake stroke of the other piston. The dead spot in the HPLC pump intake flow results from there being 30° of camshaft angular position between the points at which the pistons change, respectively, from intake to discharge and discharge to intake. The sharp transitions between the on-set of intake flow and intake flow cut-off result from the use of check valves on the intake line to each piston cylinder, as is indicated in the diagram of FIG. 1. As diagrammed in FIG. 3A, the magnitude of pump intake flow during the intake stroke of each piston exceeds the magnitude of pump discharge flow. In this way a net liquid head is built within the pump to compensate for the dead spots in pump intake flow.

In FIG. 3B, a diagram is presented of the variation of column pressure with time. It will be observed from considering FIGS. 3A and 3B in conjunction that when each piston changes from its intake stroke to its discharge stroke a transient drop in column pressure will occur. Essentially, however, HPLC pump 20 provides a constant flow at constant pressure to column 10.

Returning now to FIG. 1, solvent mixing apparatus 30 includes three solvent metering pumps identified as metering pump A, metering pump B and metering pump C, with the alphabetic designation corresponding to the particular solvent that flows through the pump. Each metering pump is identical and is indicated to include a stepper motor mechanically coupled to a reciprocating piston. Each pump further includes intake and discharge flow line check valves. Each metering pump provides a flow of its respective solvent at a rate dependent upon its speed.

The solvent flow from each metering pump is directed into a means for combining the individual solvent flows into a solvent mixture of a total flow approximately equal to the sum of the individual solvent flows. As shown in FIG. 1, the solvent combing means 32 may suitably be a flow line "X" connector fitting having first, second and third flow line legs designated by the reference numerals 34, 36 and 38, respectively, and a single output flow line 39. If only two solvents are required to be mixed, only two metering pumps would be necessary and the solvent flow combining means could be implemented with a "T" flow line connector fitting. A mixing chamber may be substituted for flow line connector fitting 32 to provide an equivalent means for performing the function.

Figure 4:
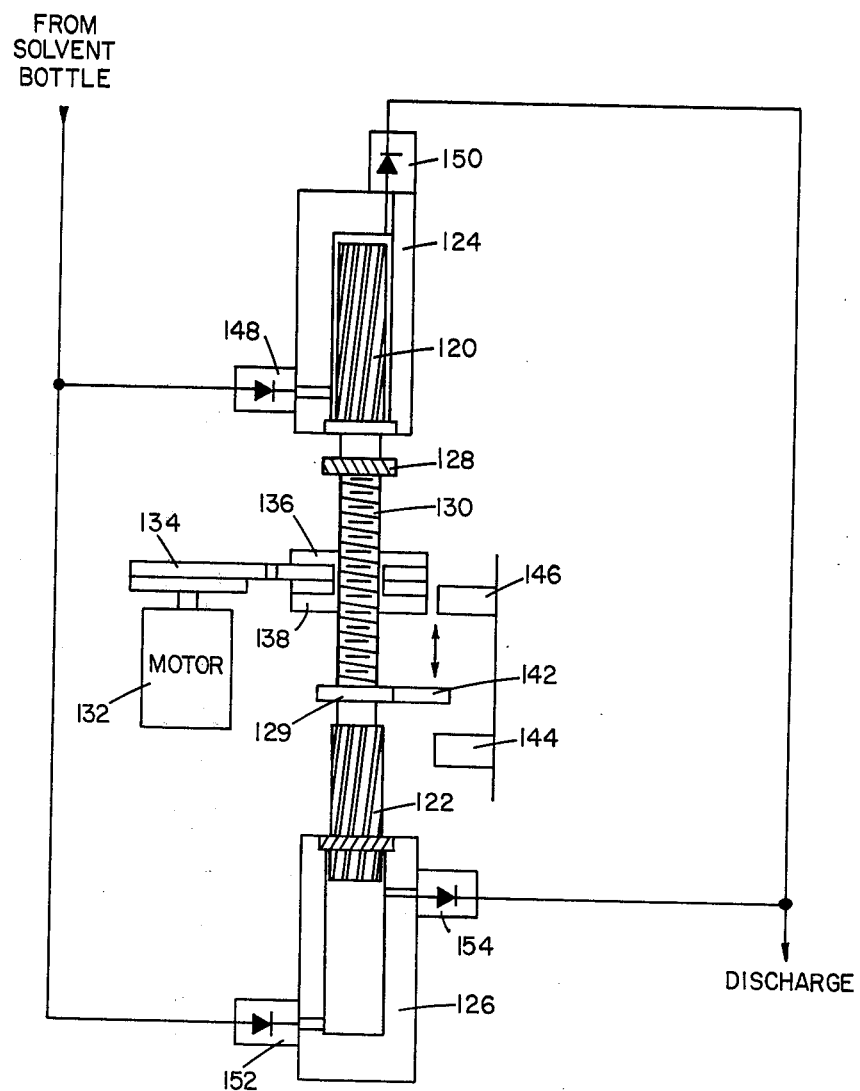
FIG. 4 is a drawing of a stepper motor driven pump for use in the solvent mixing apparatus diagrammed in FIG. 1.

Referring to FIG. 4, a representative one of the three metering pumps of solvent mixing apparatus 30 in FIG. 1 is detailed. The metering pump is a dual piston, reciprocating pump comprising first and second pistons 120 and 122. Each piston reciprocates wihtin its respective cylinder block 124, 126. The two pistons are each connected to a threaded shaft 130 through respective slip couplings 128, 129 which prevent rotation of shaft 130. The drive shaft 130 is driven in a linear reciprocating manner by stepper motor 132 coupled to drive shaft 130 by timing belt 134. The drive shaft is moved in a linear reciprocating manner as the threaded lead nut is rotated in stationary blocks 136, 138 adjacent each side of the timing belt coupling to the drive shaft. Coupling 129 carries a flag 142 for tripping optical position sensors 144 and 146 at the end of the forward and reverse strokes of the pump.

The cylinder bore in each cylinder block is slightly larger in diameter than the piston to allow for free movement of the piston and solvent mixture therein. Conventional ball and seat check valves 148, 150 and 152, 154 are provided at the intake and exhaust ports of each cylinder block as indicated. The check valves direct solvent mixture in and out of the pump and provide a sweeping effect through the cylinder. The check vlaves also prevent back flow into the pump when it is at zero flow and other interconnected pumps are pumping.

The composition of the solvent mixture provided from solvent mixing apparatus 30 will depend upon the relative speeds of the metering pumps. For example, if all three pumps are operated at equal speed, the solvent mixture provided will be composed of equal solvent proportions (i.e., 33.3% of each). If, however, the speed of metering pump A is one-half the speed of metering pump B and one-third the speed of metering pump C, in the solvent mixture produced, composition will be 16.6% solvent A, 33.3% solvent B and approximately 50% solvent C.

By changing the speeds of the pumps synchronously and in like proportion, the composition of the solvent mixture will remain the same; but, the total flow rate will be changed. For example, if the speed of all three metering pumps is doubled, the solvent mixture flow rate will similarly double. If the speed of each pump is reduced by one-half, the total solvent mixture flow rate will be decreased to one-half its previous value.

Each metering pump stepper motor is actuated for operation by a respective driver circuit 72A, 72B and 72C in controller 70. Each drive circuit receives a train of pulses and in response produces drive pulses suitable for the stepper motor. The rate of repetition of the pulses applied to each stepper motor determines the speed of the motor, and thus the speed of a respective pump.

Pulses applied to each driver circuit are derived from pulse generator 74 and a respective rate multiplier 76A, 76B or 76C for each driver circuit. Each rate multiplier performs variable-rate frequency division of the pulse train produced by pulse generator 74. That is, for a given number of pulses from pulse generator 74, a certain number of pulses will be output. The division factor applied to the pulse generator pulse train by each rate multiplier depends upon the digital word input to each device. For specific digital word inputs, each rate multiplier device performs a particular frequency division. Thus, by an appropriate digital word input to each rate multiplier, particular pulse repetition rates may be applied to each motor drive circuit. By way of example, and considering a solvent mixture of 16.6% solvent A, 33.3% solvent B and approximately 50% solvent C, such that the relative pump speeds should have pump A running at one-third the speed of pump C and one-half the speed of pump B, the pulse train from pulse generator 74 should be multiplied by a percentage factor of 16.6% in rate multiplier 76A, multiplied by a percentage factor of 33.3% in rate multiplier 76B, and multiplied by a percentage factor of 50% in rate multiplier 76C.

The digital words input to the rate multipliers are obtained from microprocessor 78. The advantages attendant to use of microprocessor-controlled HPLCs are recognized. A microprocessor-based controller readily permits the creation and storage of complex gradient profiles. Operator commands for controlling the entire chromatographic system are initiated by keyboard 77. Through the keyboard, such parameters as flow rate, solvent selection and run time are set. In response to operator specification of the parameters on the keyboard, the microprocessor generates the appropriate digital word to each of the rate multipliers. In addition, the microprocessor generates and sends a digital word to digital-to-analog converter 79. An analog voltage signal is produced by digital-to-analog converter 79 equivalent to the digital word input. The voltage is applied to an amplifier 71 which increases the D/A converter output to a some predetermined greater level, typically 20% greater, for a reason to be explained. The voltage from amplifier 71 is applied to pulse generator 74 to establish the pulse repetition rate. The voltage from amplifier 71 is also applied to amplifier 73 which provides a voltage input to the pump drive of HPLC pump 20 to establish its speed of operation. Amplifier 73 applies a fractional gain (i.e., a gain less than 1, and typically 0.4) to provide a voltage level within the speed range of the HPLC pump.

The flow of solvent mixture in flow line 39 is received into detector cell 80 in an input supply flow. Solvent mixture is withdrawn from detector cell 80 through flow line 41 by intake strokes of HPLC pump 20 in an output flow corresponding to the HPLC pump intake flow diagrammed in FIG. 3A. By proper setting of the repetition rate of pulse generator 74, which is established by the output voltage of amplifier 71, the solvent mixing apparatus is deliberately allowed to run at a speed which provides a greater flow rate (typically 20% more as determined by the gain of amplifier 71) into detector cell 80 than the intake flow rate of the HPLC pump. As a result, a volume amount of solvent mixture will accumulate in detector cell 80, with the volume amount being dependent upon the relative rates of cell input and output flow. A small overflow 82 to waste container 84 is also indicated.

Detector cell 80 senses the volume amount of solvent mixture accumulated and continuously produces an output indication of the accumulated solvent mixture volume.

Suitably, detector cell 80 is an electrical measurement device for measuring an electrical property of the solvent mixture that varies as a function of volume amount. Preferably, detector cell 80 is an electrical admittance measurement device. However, numerous other liquid level detection techniques and devices can be utilized. For example, optical sensing is a possible alternate detection scheme. A temperature or pressure sensitive transducer could be utilized. Another possibility is the use of a flexible diaphram with strain gauges or a linear-variable differential transformer.

In using electrical admittance measurement as the liquid level or volume sensing technique for determining the relative rates of flow at which solvent mixture is being provided by solvent mixing apparatus 30 and demanded by HPLC pump 20, a means of providing electrical excitation for the detector cell is required. This may suitably be provided by a square wave oscillator 86.

Figure 5:
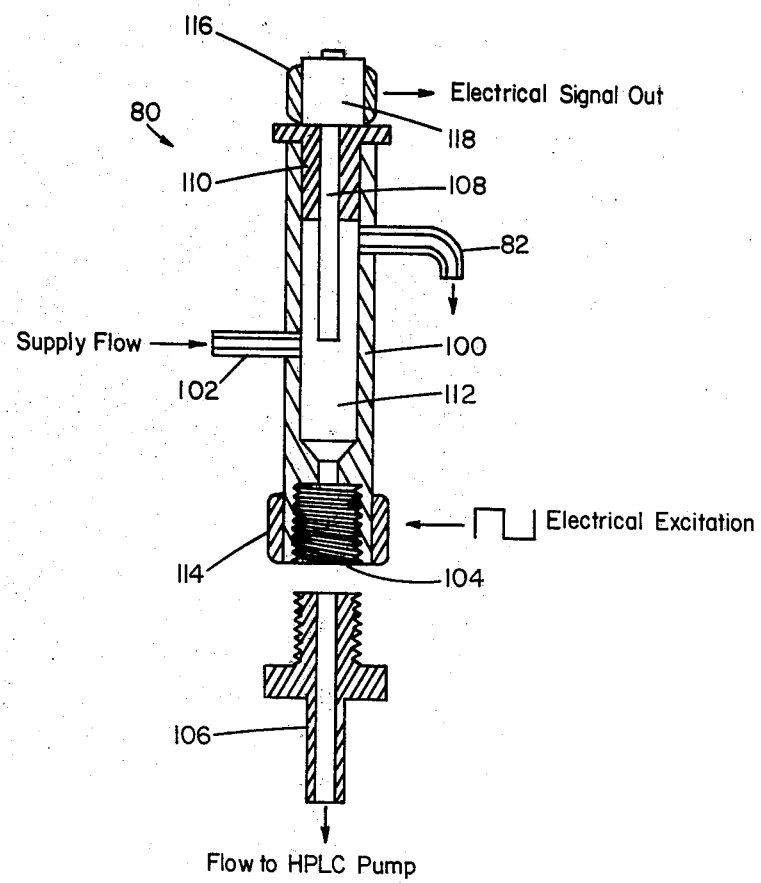
FIG. 5 is a diagram in cross-section of the admittance measurement cell shown in FIG. 1.

Referring to FIG. 5, there is presented a detailed cross-section drawing of an electrical admittance measurement cell for use as the detector cell in FIG. 1. The admittance detecting cell comprises a cylindrical barrel or chamber 100 of stainless steel. The liquid volume of the cell chamber is approximately 130 microliters. A tubing connection 102 at a point intermediate the ends of chamber 100 as shown provides an inlet supply flow port for connecting with flow line 39 in FIG. 1. The lower end of chamber 100 has internal threads 104 for receiving therein a tube fitting 106 which defines an outlet port for connection to flow line 41 leading to the intake of HPLC pump 20 in FIG. 1. An overflow vent pipe 82 is disposed at the top of the cell chamber. A reservoir is defined between the inlet and outlet ports into which solvent mixture may accumulate.

A solid stainless steel rod 108 is mounted concentrically in the center of chamber 100 and insulated therefrom by insulator 110. The body of chamber 100 serves as the excitation electrode and rod 108 constitutes a sensing electrode. Electrical excitation applied to the cell chamber body is sensed by the sensing electrode through the resistance and dielectric of the solvent mixture material accumulated in the reservoir space 112 betwen inlet port 102 and outlet port 106. Electrical connections are made to the admittance cell by metal springs clips 114 and 116. Clip 114 frictionally grips cell chamber body 100, and clip 116 frictionally clips the enlarged external end 118 on rod 108.

Figure 6A:
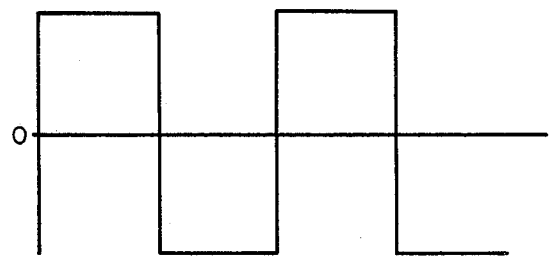
FIGS. 6A–6C are waveform diagrams representing admittance measurement cell applied excitation and excitation response signals for solvent mixtures of high conductivity and high dielectric strength.
Figure 6B:
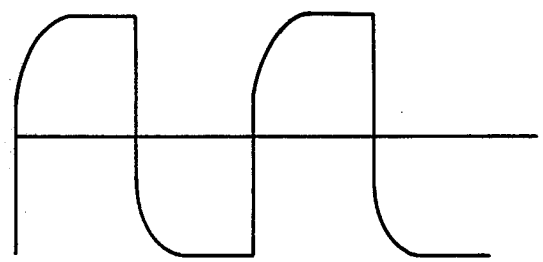

The electrical cell excitation signal may be a bipolar square wave signal as shown in FIG. 6A is utilized. If the conductivity of the solvent mixture is high, the detector cell response will be as shown in FIG. 6B. But if the solvent mixture in the chamber is of high dielectric (i.e., low conductivity), the spiked waveform of FIG. 6C will be the response. Regardless of the electircal characteristics of the solvent mixture in the chamber, the amplitude of the response signal rise will be functionally related to the volume amount of solvent mixture accumulated in the cell chamber.

Figure 7:
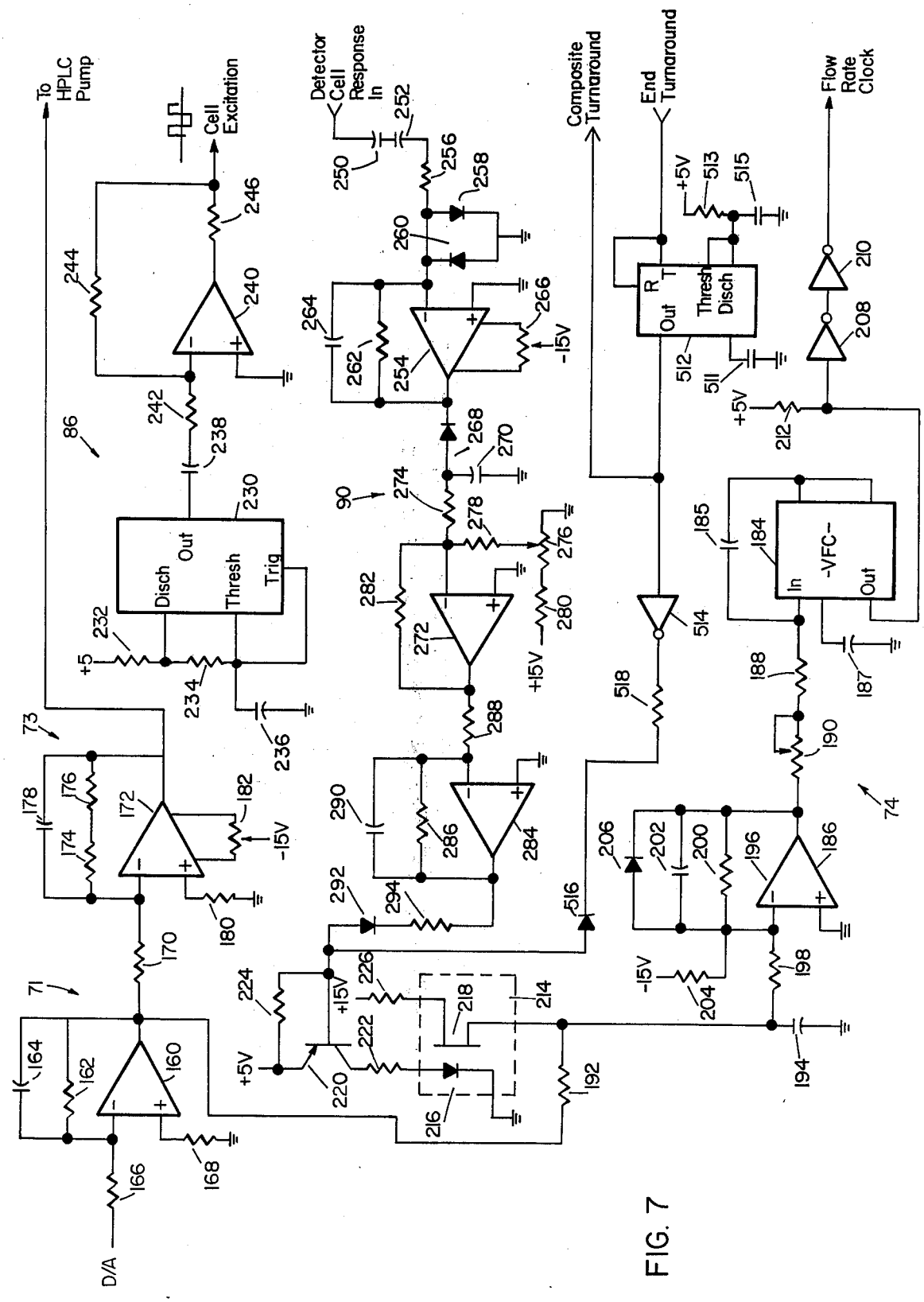
FIG. 7 is a detailed schematic diagram of electronic circuitry implementing the electrical control circuit diagrammed in FIG. 1.

Referring to FIG. 7, electronic circuitry for implementing electrical control circuit 90 is schematically diagrammed. However, as well, pulse generator 74 and amplifiers 71 and 73 are also presented, and these will be described first.

Amplifier 71 comprises an operational amplifier 160 having a feedback network of resistor 162 and filter capacitor 164. An input resistor 166 connects to the inverting input of operational amplifier 160 and receives the output voltage of the digital-to-analog converter. The non-inverting input of operational amplifier 160 is referenced to ground through resistor 168. The values of resistors 162 and 166 are chosen to provide a gain of something greater than one. Preferably, the gain of amplifier 71 is approximately 1.2. The digital-to-analog converter output voltage is scaled to correspond to a total solvent mixture flow rate of one milliliter per minute for each volt. Accordingly, the gain factor of 1.2 through amplifier 71 establishes the actual solvent mixture flow rate from the solvent mixing apparatus at approximately 20% higher than the level set by the microprocessor through the digital-to-analog converter.

The output of amplifier 71 is split along two circuit paths. One of the circuit paths leads to amplifier 73 through input resistor 170. Amplifier 73 comprises an operational amplifier 172 having a feedback network of resistors 174, 176 and filter capacitor 178. The non-inverting input is reference to ground through resistor 180 and an offset adjustment potentiometer 182 is provided. Amplifier 73 applies a fractional gain, that is a gain less than one, to the voltage from amplifier 71. The reduction in voltage establishes a signal level within the voltage range for proper operation of the HPLC pump drive. HPLC pump 20 in FIG. 1 produces one milliliter per minute of liquid flow to column 10 for each one-half volt of the input signal to the HPLC pump drive circuit (i.e., 0.5 v/ml/min.).

The second path for the output of amplifier 71 is to pulse generator 74. A voltage to frequency converter (VFC) 184 produces a pulse train at a repetition rate dependent upon the input voltage applied thereto. The actual voltage input to VFC 184 is derived from a filter/buffer circuit 186 connected to VFC 184 by resistor 188 and potentiometer 190.

Since the solvent metering pump drive motors are stepping motors that run at a speed proportional to frequency, because of inertia the motors must be accelerated up to speed and decelerated to stop, the output pulse repetition rate from VFC 184 is required to build up to the final pulse repetition rate and decrease to zero over a period of time. In order to produce an output square wave pulse train that ascends and decends in frequency, a ramp-up and ramp-down input voltage, for each respective operational condition, is required. Filter/buffer circuit 186 provides such ramp voltage input.

The acceleration rate is set by the time of constant established by the series combination of resistor 192 and capacitor 194. If a step change is made in the output voltage of the digital-to-analog converter, producing a step change in the output voltage of amplifier 71, the voltage change on the inverting input of operational amplifier 196 is a ramp rather than a step voltage change. The inverting input of operational amplifier 196 is connected to the RC time constant network by resistor 198. Buffer circuit 186 further includes a feedback resistor 200 and a high frequency filter capacitor 202. A minus bias voltage is applied to operational amplifier 196 by resistor 204. A limiting diode 206 is further included in the feedback loop of the buffer circuit.

The output pulse train of VFC 184 is output as the flow rate clock to the rate multipliers (as shown in FIG. 1) through an output drive circuit of inverters 208, 210 and pull-up resistor 212.

Operation of the solvent metering pumps can, of course, be discontinued by generation of an appropriate output from the microprocessor which acts through the digital-to-analog converter and the circuitry already described. However, it is also necessary to decelerate and subsequently accelerate the stepper motor when the reciprocating drive shaft of the pump has advanced to the end of its stroke. This point can be referred to as the "end-turnaround point." Also, as will be explained more fully later, the solvent metering pumps are synchronously stopped and started by a control input from electrical control circuit 90 in FIG. 1.

In order to turn-on and turn-off the solvent metering pumps in either of the later two situations, a control input must be provided into the pulse generator circuitry. This is accomplished as shown in FIG. 7 by use of an optocoupler 214 connected to the interconnection point of resistor 192 and capacitor 194. The optocoupler includes a light emitting diode 216 and a field effect transistor 218 which acts as a variable resistance. Light emitting diode 216 of the optocoupler is connected in series with switching transistor 220 with a current limiting resistor 222 being inserted inbetween. A resistor 224 is connected between the base of transistor 220 and +5 volts to maintain cut-off of transistor 220 until the base is pulled negative with respect to 30 5v, whereupon the transistor will switch to a conducting state, Field effect transistor 218 is connected in series with an external resistor 226 tied to +15 volts.

When light emitting diode 216 is not forward biased, there is no light output and the resistance of transistor 218 is extremely high so as to isolate the connection of resistor 192 and capacitor 194. However, when transistor 220 is switched to a conducting state, light emitting diode 216 will be forward biased and current flow therethrough will produce light sensed by transistor 218. The resistance of transistor 218 is then reduced to a negligible amount. This allows resistor 226 to become a charging source to the connection point of resistor 192 and capacitor 194, which is pulled up to 30 15 volts. The minus bias placed on the inverting input of operational amplifier 196 would in the absence of the control input of the optocoupler maintain the output of amplifier 196 at a level above zero volts even though the output voltage of amplifier 71 has been placed at zero. The control input provided by optocoupler 214, however, when activated drops the output voltage of amplifier 196 through zero.

Electrical cell excitation for detector cell 80 is obtained from square wave oscillator 86. One implementation of the oscillator is shown in FIG. 7 and comprises a timer circuit 230 operating as an astable multivibrator. The frequency output is determined by external timing components of resistor 232, resistor 234 and capacitor 236. The output signal is coupled by d.c. blocking capacitor 238. The output of timer circuit 230 is a unipolar waveform with excursions between zero volts and 5 volts. Since the cell excitation is preferably a bipolar drive signal, the output of timer circuit 230 by coupling through capacitor 238 produces a bipolar spiked waveform. The signal coupled through capacitor 238 is applied to a high gain amplifier circuit comprising operational amplifier 240. The signal is input through input resistor 242. A feedback resistor 244 is included in the circuit along with an output resistor 246. The gain of amplifier 240 is established sufficiently high to saturate the output of the amplifier and provide a bipolar square wave signal.

Figure 6C:
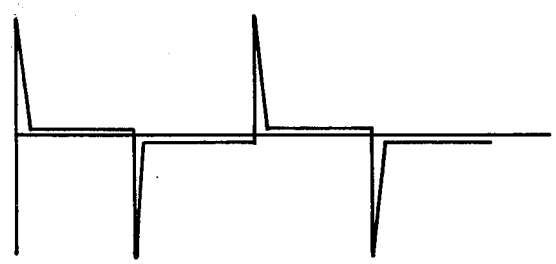

As already described in connection with FIGS. 6A-C, in response to the bipolar square wave cell excitation, an output response signal is available from detector cell 80, and is input to electrical control circuit 90. As shown in FIG. 7, the signal is coupled through d.c. blocking capacitors 250, 252 to an amplifier circuit comprising operational amplifier 254. The signal is applied to the inverting input through an input network comprising input resistor 256 and a pair of protective diodes 258, 260. The feedback network includes resistor 262 and capacitor 264. An offset adjustment potentiometer 266 is also included.

The output of amplifier 254 will be a duplication of the detector cell response signal. This signal will thus contain information regarding the electrical admittance of the solvent mixture material. That is, both the electrical conductivity and electrical susceptance characteristics of the material will be represented in the waveform. And again, the rise of the signal level, or the peak, will be representative of the volume amount of solvent mixture accumulated in the cell chamber. Since information regarding the volume amount of solvent mixture in the cell is of interest, the output signal from amplifier 254 is peak detected using diode 268 and capacitor 270.

The voltage developed on capacitor 270 is applied to a comparator circuit comprising operational amplifier 272. The input network to the inverting input includes a resistor 274 connected to capacitor 270, and further includes a combination of potentiometer 276 and resistors 278 and 280. The wiper of potentiometer 276 will have a positive voltage thereon. If the negative level on the peak detector exceeds in magnitude the voltage level on the wiper of potentiometer 276, the output of amplifier 272 will go positive. Until the negative level on the peak detector exceeds the positive level on the wiper of potentiometer 276, the output of amplifier 272 will be maintained at zero volts or at a negative voltage. A feedback resistor 282 is also included.

The comparator circuit provides a means for developing a voltage representative of a reference solvent mixture volume amount against which the actual solvent mixture volume amount in the cell can be evaluated.

The output of amplifier 272 is applied to a high gain amplifier stage comprising operational amplifier 284, feedback resistor 286 and input resistor 288. A small capacitor 290 is also included for filtering. When the output of amplifier 272 goes positive, the output of amplifier 284 will go negative. By reason of the interconnection of the output of amplifier 284 to the base of switching transistor 220 through diode 292 and resistor 294, when the output of amplifier 284 goes negative, transistor 220 will be turned on. This will, of course, turn on drive current through optocoupler 214 and shut-down the flow rate clock which will in turn inhibit operation of the solvent metering pump stepper motors.

If the accumulated volume amount of solvent mixture in detector cell 80 falls to a level such that the resulting response signal is of an amplitude when peak detected that is less than the reference voltage level set on potentiometer 276, transistor 220 will be switched off, and the solvent metering pump stepper motors will be enabled for operation and will accelerate back up to the speed prescribed therefor by the output of amplifier 71.

Figure 8:
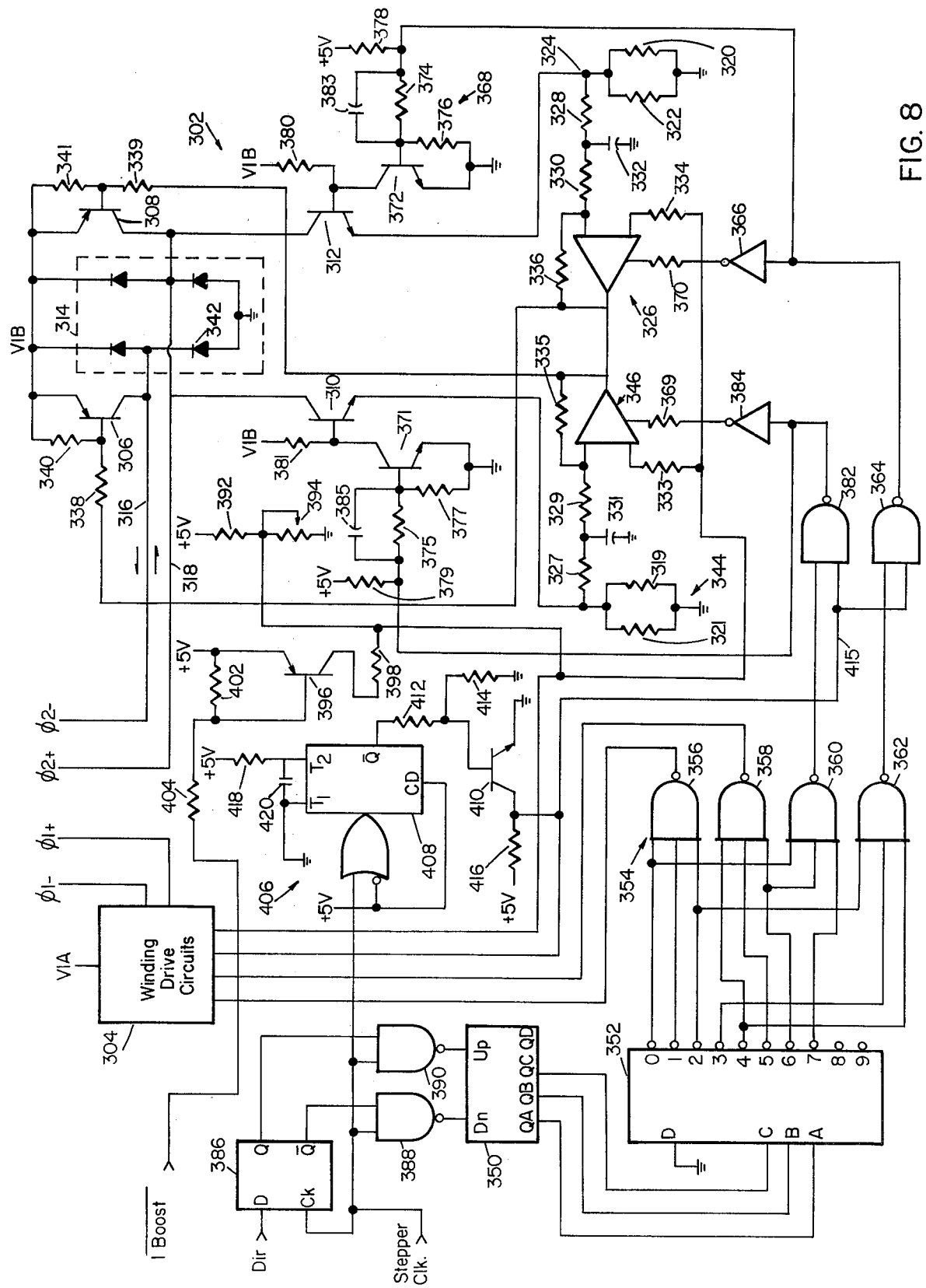
FIG. 8 is a detailed schematic diagram of electronic circuitry implementing the motor drive circuits diagrammed in FIG. 1.

Referring now to FIG. 8, a schematic diagram for a representative one of the drive circuits 72 in FIG. 1 is diagrammed. The driver circuit provides bipolar drive to a stepper motor. That is, each winding in the motor is being energized in two polarities. Rather than using both positive and negative power to provide bipolar drive, each winding of the motor is placed in a bridge network. In the diagram of FIG. 8, two identical bridge network circuits and an energization sequence control circuit are diagrammed. A separate bridge network circuit is required to drive each motor winding; however, only one of the two identical bridge network circuits is diagrammed in detail. That one is indicated by the reference numeral 302. The other identical bridge network circuit is indicated by a rectangle with the reference numeral 304. Winding drive circuit 304 drives winding #1 of a stepper motor, and winding drive circuit 302 drives winding #2 of the motor.

Referring now specifically to bridge network circuit 302, motor winding #2 is connected in a bridge network circuit comprising transistors 306, 308, 310 and 312. A diode bridge 314 is connected into the circuit to provide diode protection for each transistor against winding reverse current induced voltage spikes.

The side of the bridge network that is common with the collectors of transistors 306 and 310 ties to one end of motor winding #2. The other side of the bridge network that is common with the collectors of transistors 308 and 312 ties to the other end of the winding. The direction of current flow through the motor winding is dependent upon which of the transistors are turned on. For current flow through motor winding #2 from end $\phi 2-$ to end $\phi 2+$, transistors 306 and 312 must be turned on. For current flow in the opposite direction from end $\phi 2+$ to end $\phi 2-$, transistors 308 and 310 must be turned on.

Assuming for purposes of discussion that transistors 306 and 312 are turned on, and further assuming conventional current notation of current flowing from positive to negative, current will be flowing to motor winding #2 through conductor 316 in the direction of the arrow and flowing from motor winding #2 in conductor 318 in the direction of the arrow. Current flowing through transistor 312 comes down through the parallel combination of resistors 320, 322 which forms a current sensing network. That is, the voltage at node 324 is equal to the value of the equivalent resistance of the parallel combination of resistors 320, 322 multiplied by the current flow therethrough.

The voltage on the current sensing network is applied to comparator circuit 326. The voltage is input to the non-inverting input of the comparator through an input network of resistor 328, resistor 330 and capacitor 332. A reference voltage derived in a manner to be described is applied to the inverting input of the comparator through resistor 334. A feedback resistor 336 sets the gain of the circuit. The output of comparator 326 cross-ties to the base of transistor 306 through resistor 338. Another resistor 340 connects to the base of transistor 306 to maintain transistor 306 in cut-off until an output condition on comparator 326 is established for turn-on.

If the current flowing through winding #2 of the motor is of sufficient magnitude to produce a voltage on the non-inverting input of comparator 326 that exceeds the reference voltage on the inverting input, the output of comparator 326 will be high, which turns transistor 306 off. With transistor 306 turning off, the current path through the winding of the motor is broken. However, since the winding of the motor is an inductive device, current therethrough cannot be discontinued instantaneously. Accordingly, diode 342 in network 314 supplies a current path to maintain current through the winding until it can decay through its normal RL time constant.

As the winding current decays, the voltage across the sensing network decreases. When the voltage gets below the threshold reference level set on the comparator, the output of comparator 326 goes low, causing transistor 306 to turn back on. The current sensing network and comparator combination rapidly switches transistor 306 on and off with the time-average of the current flowing through the motor winding being of the desired value. There is some hysteresis built into comparator 326, so that the highest frequency of oscillation is held within a permissible limit.

Current flow in the opposite direction through the motor winding is achieved in a similar manner. In that circumstance, transistors 308 and 310 are conducting and establish current flow through current sensing network 344. The output of a comparator circuit 346 is cross-tied to the base of transistor 308, and the same reference voltage that is applied to the inverting input of comparator 326 is applied to the inverting input of comparator 346.

Stepping of a stepper motor involves sequentially energizing the coils. Moreover, the sequence of energizing the motor coils is unique for each particular stepper motor. Thus, sequence control logic is further included in the driver circuit and designed for the sequence necessary for a Sigma 17-2220D200-B016.

Sequencing of the bridge network circuits 302 and 304 for proper sequential energization of the windings of the stepper motor connected as indicated to the bridge, is provided by digital logic circuitry providing the necessary sequencing signals to the winding drive circuits. This logic includes a binary up/down counter 350, the binary count of which is applied to a one-of-ten decoder 352, which is indicated to have negative true outputs. That is, all outputs are a logic one except that output whose corresponding binary code appears on the input from counter 350. Thus, using only the three bits indicated, as binary counter 350 counts, the single logic zero output of decoder 352 sequentially steps between output 0 and output 7. If the counter is counting up, the sequencing is a loop from output 0 to output 7 and back to output 0. However, if the counter is counting down, the sequencing is from output 7 to output 0, and then a jump back to output 7. Therefore, as a function of the direction in which the counter is counting, a logic zero travels across the output lines of decoder 352.

The outputs of decoder 352 are applied to decode logic 354 which comprises four 3-input NAND gates 356, 358, 360, and 362. The outputs of decode logic 354 are used to enable winding drive circuits 302 and 304 in the proper sequence for energizing the motor. For purposes of illustration, consider NAND gate 362 of the decode logic. If a point in the binary count is reached which establishes output 2 of decoder 352 a logic zero, the output of NAND gate 362 is a logic one. This signal is supplied as one input to NAND gate 364. Assuming that the other input to NAND gate 364 is also a logic one, a logic zero output will be produced which is applied to inverter 366 and transistor circuit 368. The output of inverter 366 will then be a logic one. The output of inverter 366 is applied through resistor 370 as a strobe input to comparator 326. Prior to the output of NAND gate 364 going to a logic zero condition, the output of inverter 366 is low. A low strobe input to comparator 326 places the output of comparator 326 high, where it is maintained regardless of the input conditions. But, when the strobe input is taken high, the comparator output responds to the input conditions. If the conditions warrant it, the output of comparator 326 may go low, turning on transistor 306.

Transistor circuit 368 comprises transistor 372 and a base lead input network of resistors 374 and 376. Prior to the time the output of NAND gate 364 goes low, the input network places transistor 372 in a conducting state. This pulls down the base of transistor 312 and keeps it in a nonconductive state. A pull-up resistor 378 maintains the input line to the transistor circuit high until the output of NAND gate 364 goes low.

When the output of NAND gate 364 does go low, transistor 372 is turned off, releasing the base of transistor 312. Drive current through resistor 380 is applied to the base of transistor 312 placing it into conduction, which enables current flow through motor winding #2 in the direction of the arrows adjacent lines 316, 318, provided the conditions at the inputs of comparator 326 warrant current flow.

At the appropriate points in the stepping motor drive sequence, the output of NAND gate 382 will go low, driving the output of inverter 384 high. This enables comparator 346 for operation. Also, the output of NAND gate 382 results in transistor 310 being turned on to enable current flow in the opposite direction through the motor winding.

The decode logic 354 is arranged such that current drive through the coil in only one direction is possible at any one time, which is, of course, what is desired. Furthermore, the sequencing established by decoder 352 provides for operation of the motor in what is known as "half-stepping." That is, the motor is driven such that it moves in increments of only half the distance of a full step. Whereas in full-stepping of the motor, both windings of the motor are energized, in half-stepping, time periods are set up during which only one motor winding is energized, with the other one being deenergized.

The direction that the motor turns is a function of the sequencing of the current flow through the windings. In sequence control logic shown, if the rippling logic zero on the output of decoder 352 is going from output 0 to output 7 and then looping back to output 0, the motor turns in one direction. On the other hand, if the rippling zero sequence is from output 7 to output 0 and loops back to output 0, the motor goes in the opposite direction. The direction in which the rippling zero at the output of decoder 352 is looping, as explained previously, depends upon whether counter 350 is counting up or counting down. Up/down control of counter 350 is provided by logic comprising a D flip-flop and NAND gates 388, 390. A direction input bit (DIR) is clocked through either the Q or $\overline{Q}$ output to enable clock pulses to be gated through to either the count up input or the count down input of counter 350. The direction input comes from the stepper motor logic in FIG. 9, as does the stepper clock input.

The reference voltage applied to comparator 326, 346 is derived from a voltage divider network of resistor 392 and potentiometer 394. Also connected to the reference voltage line is a circuit comprising transistor 396, the collector of which is connected to the reference voltage line by resistor 398. An emitter resistor 400 and bias resistor 402 are also included. By controlling the conduction of transistor 396, the reference voltage to the comparators may be varied. If a signal I Boost is pulled low, which will take the base lead of transistor 396 low through resistor 404, transistor 396 will turn-on and raise the reference voltage level to the comparators. It may be desirable to raise the voltage level on the comparators, indicating a higher motor reference current, when the motor reverses direction in order to supply a little more current to the motor as it is accelerating back up to normally operating speed.

The common logic input to NAND gates 364, 382 is provided by an enabling circuit 406 receiving stepper clock pulses. This circuit is included to remove excitation from the motor when its movement is not needed. It is possible to keep current excitation up, but if that is done, additional heat is generated. The removal of power from the motor is possible in the present application since the pump driven by the motor will not be subject to movement and does not, therefore, require a force to hold position.

Circuit 406 is built around one-shot 408. As long as a clock is coming in regularly, the one-shot is continuously triggered and the $\overline{Q}$ output is kept low. The $\overline{Q}$ output is connected to a transistor 410, the collector of which is connected to one of the inputs on each of NAND gates 364, 382. A voltage divider network of resistors 412, 414 is connected to the $\overline{Q}$ output of one-shot 408, with the tap point of the voltage divider being connected to the base lead of transistor 410. A load resistor 416 is connected in the collector circuit of transistor 410 and maintains a high condition, or a logic one, on each of the inputs to NAND gates 364, 382. If there is an absence of a clock pulse within a certain period of time, as determined by the external timing components of resistor 418 and capacitor 420 connected to one-shot 408, the one-shot "times out" and the $\bar{Q}$ output goes high. This will turn-on transistor 418, pulling line 415 low and disabling NAND gates 364, 382. Although not critical, the time-out period for one-shot 408 is suitably approximately one to two seconds. As soon as a clock pulse is received, the NAND gates are enabled and the circuit is back up and running.

Figure 9:
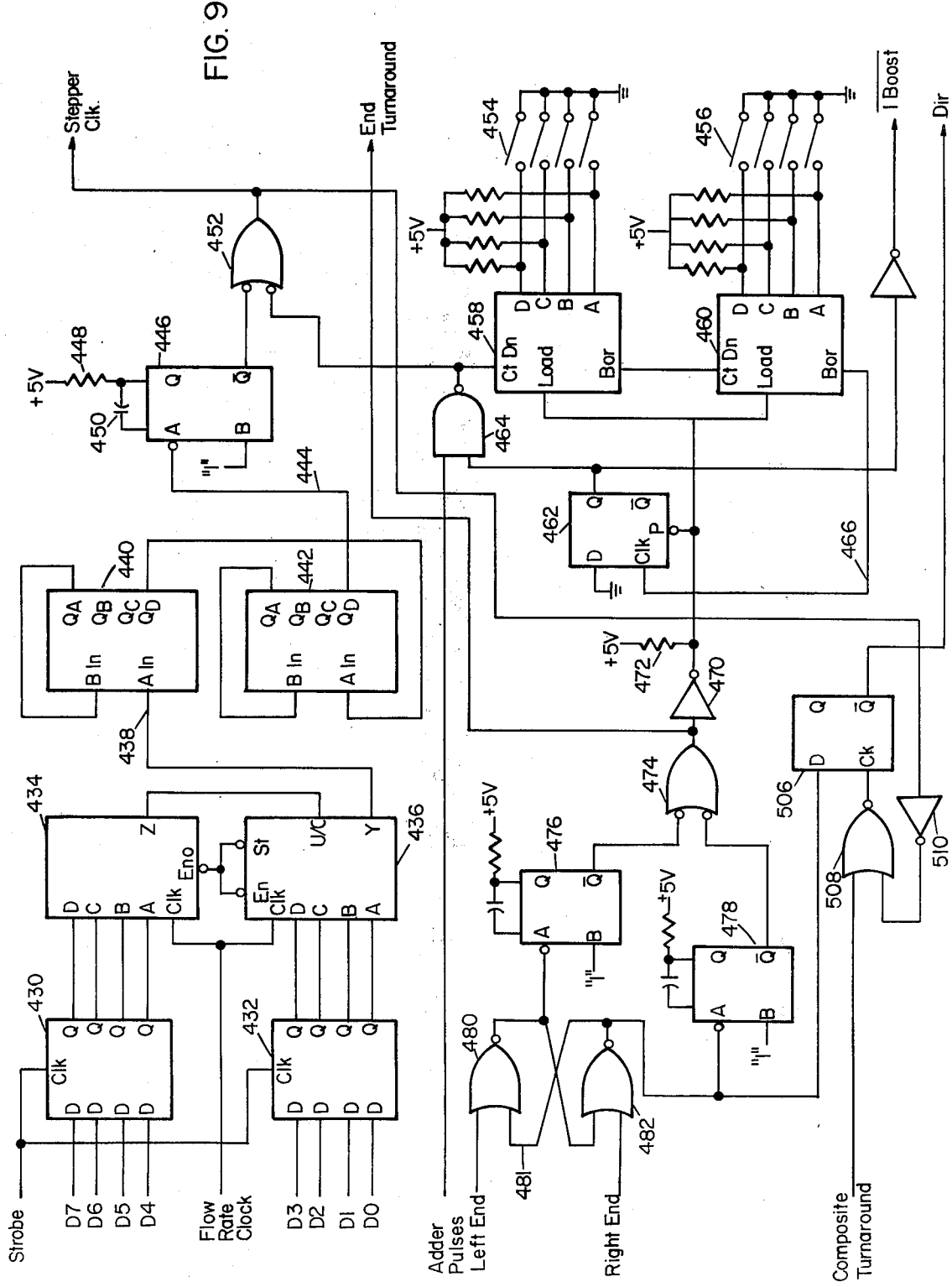
FIG. 9 is a detailed schematic diagram of electronic circuitry implementing the rate multiplier function diagrammed in FIG. 1.

Turning now to FIG. 9, the signals Stepper Clk, I Boost, and the motor direction signal DIR are obtained from the stepper logic shown in this schematic diagram. The stepper logic receives a digital word input from the microprocessor and also receives the Flow Rate Clock from the pulse generator circuitry in FIG. 7. The digital input from the microprocessor is in the form of two 4-bit binary coded decimal (BCD) words. The two BCD words are received as data bits D0-D3 for the first word and as data bits D4-D7 for the second word. Each BCD word is one of two digits in a number that expresses the desired percentage of the respective solvent to be in a solvent mixture produced by the solvent mixing apparatus. The value may be from 0-99%.

The data bits D0-D7 are set up by the microprocessor at the inputs of two quad D flip-flop devices 430, 432. The data bits are entered by a signal Strobe from the microprocessor and applied to the clock input of devices 430 and 432. The data bits representing the two BCD words appear at the Q outputs of devices 430, 432 which are connected to decade rate multipliers 434, 436. The rate multipliers are cascaded to perform two-decade rate multiplication. The input clock signal to the rate multipliers is Flow Rate Clock. The two-decade rate multiplication function provided by rate multipliers 434, 436 performs a frequency division on the Flow Rate Clock, such that for every 100 pulses of Flow Rate Clock a certain number of clock of pulses will be produced on the output line 438.

Because the rate multipliers do not produce an output waveform with the pulses evenly spaced, and even spacing is desired, the rate multiplier output signal on line 438 is applied to two cascaded counters 440, 442. The counter outputs provide evenly spaced signals, but these devices in combination provide an additional divide by one hundred frequency division which must be taken into account in setting the pulse repetition rate of the pulse generator. Furthermore, the output of decade counter 442 has a pulse width that is a function of the counting frequency; and because the frequency at which it is operating will change from time to time with changes in the desired speed for the respective pump, the pulse width of the output signal on line 444 will be variable. In order to obtain a narrow, fixed-width pulse, the output of decade counter 442 is applied to a one-shot device 446 having external timing components of resistor 448 and capacitor 450 which set the pulse width. The narrow, fixed-width pulse from one-shot 446 is available from the $\bar{Q}$ output and is passed through OR gate 452 to form the Stepper Clk.

Stepper Clk may also be provided by a second input to OR gate 452. This second input to gate 452 is a signal from the microprocessor labeled "Adder Pulses." Because of mechanical backlash in the motor coupling to the pump drive shaft, a degree of inaccuracy exists in the operation of the pump, which would result in a corresponding error in the solvent mixture produced.

The backlash problem manifests itself at the time of turnaround, or motor reversal. The scheme then is to insert added pulses into the Stepper Clk output to the drive circuit at the time of motor reversal. This operation is accomplished by the circuitry in the lower portion of the drawing in FIG. 9.

The desired number of pulses to be given the motor at turnaround is set by switches 454 and 456. Closure of selectted ones of the switches in each grouping establishes a binary code input to up/down counters 458, 460. A signal obtained in a manner to be explained loads the code set by switches 454, 456 into counters 458, 460 and also presets D flip-flop 462. Setting of flip-flop 462 enables NAND gate 464 to pass Adder Pulses through OR gate 452 and to the count-down input of counter 458. After the desired number of pulses of Adder Pulses have been sent out, counters 458 and 460 will be counted down to zero, and a signal will be issued from counter 460 over line 466, which clocks flip-flop 462. Since the D input on flip-flop 462 is tied to ground, after clocking, the Q output will be a logic zero. This disables NAND gate 464 and prohibits Adder Pulses from being applied to OR gate 452.

The setting of switches of 454, 456 is determined arbitrarily. The pumps in the solvent mixing apparatus are operated and the output of the pump is observed with a detector, and without a column. If two solvents which the detector sees as different adsorbants are being mixed, then when one pump undergoes turnaround, there will be a very pronounced spike in the trace. This is because at the time the motor is reversing, it is having to traverse the backlash distance and the pump is not pumping; and therefore the liquid composition is 100% of the solvent being flowed by the other pump. Accordingly, while observing the detector response trace, the switches are arbitrarily set to different values until the spike in minimized. The switches may have to be reset as the mechanical components of the pump wear.

The pulses to be added in, as previously stated, are obtained from the microprocessor as a clock designated Adder Pulses. The Adder Pulses clock is generated using Flow Rate Clock and a software programmable counter in the CPU of the microprocessor. A divisor to the counter is software set as a function of the set flow rate. That is, the frequency of the Adder Pulses clock is established at some particular clock rate relative to the Flow Rate Clock; and thus, it will increase and decrease in frequency in response to acceleration and deceleration of the motor. Although the Adder Pulses clock bears a proportional relationship to the Flow Rate Clock, the constant of proportionality changes as a function of the flow rate setting. This is because it is desired to apply the Adder Pulses signal to the motor at a rate corresponding to the maximum possible speed that the pump can move. Accordingly, the software set divisor for the software programmable counter in the CPU of the microprocessor changes as a function of the Flow Rate Clock to maintain the frequency of the Adder Pulses clock at a frequency corresponding to the maximum speed of the pump, which incidentally is 10 milliliters per minute. The relationship existing between the various parameters is best understood by reference to TABLE I below.

TABLE I

| Set Flow Rate (ml/min.) | Nominal Clock (pulses/sec.) | Pulse Generator (KHZ) | Adder Pulses (KHZ) | CPU ÷ Factor |
|---|---|---|---|---|
| 0 | 0 | 0 | 0 | X |
| 1 | 266.6 | 26.6 | 2.666 | 10 |
| 2 | 533.3 | 53.3 | 2.666 | 20 |
| 3 | 799.9 | 79.9 | 2.666 | 30 |
| 4 | 1066.0 | 106.6 | 2.666 | 40 |
| 5 | 1333.3 | 133.3 | 2.666 | 50 |
| 6 | 1600.0 | 160.0 | 2.666 | 60 |
| 7 | 1866.0 | 186.6 | 2.666 | 70 |
| 8 | 2133.0 | 213.3 | 2.666 | 80 |
| 9 | 2399.0 | 239.9 | 2.666 | 90 |
| 10 | 2666.6 | 266.6 | 2.666 | 100 |

In TABLE I, there is indicated the nominal clock rate to the motor for establishing the corresponding pump flow rate. In order to deliver a particular nominal clock rate, the pulse generator must deliver an appropriate clock frequency such that after the division by one hundred provided in decade counters 440, 442 in FIG. 9, the nominal clock will result. It is to be noted that this relationship does not involve a consideration of the solvent mixing proportions division factor introduced by the rate multipliers. From TABLE I, the nominal clock rate for the maximum flow rate of 10 milliliters per minute is 2666.6 pulses per second or 2.666 kilohertz. Thus, the Adder Pulses clock frequency, which is desired to be at the stepper motor pulsing rate for maximum pump speed, should be 2.666 kilohertz. For each flow rate setting, the corresponding pulse generator frequency is divided by the desired Adder Pulses clock frequency to yield the necessary CPU programmable counter division factor. As shown in TABLE I, the CPU counter division factor is merely ten times the flow rate setting.

Returning attention to FIG. 9, the signal for loading counters 458, 460 is obtained from an open collector inverter 470 having a Pull-up resistor 472 connected thereto. The input of inverter 470 is connected to OR gate 474 which receives inputs from the Q̄ outputs of one-shots 476 and 478. These one-shots are triggered by the outputs of an R-S latch comprising NOR gates 480 and 482. The set and reset inputs to the latch are the signals Left End and Right End. These two signals are obtained from optical sensors 144 and 146 shown in FIG. 6 that the end of drive shaft stroke and designate end turnaround (or reversal) of motor 132.

Figure 10:
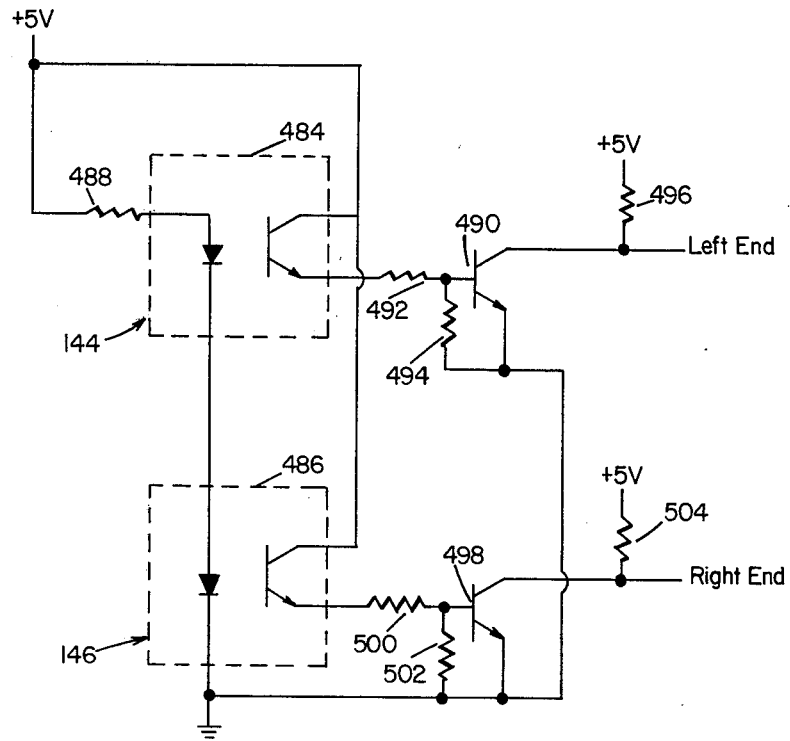
FIG. 10 is a detailed schematic diagram of an implementation of the end turnaround sensors indicated in FIG. 4.

Referring briefly to FIG. 10, there is presented a schematic diagram for an implementation of optical sensors 144 and 146. Each sensor is identical and includes a respective optocoupler device 484, 486 comprising a light emitting diode and phototransistor. The light emitting diodes of the optocouplers are connected in series with a current limiting resistor 488. The emitter of the phototransistor in optocoupler 484 is coupled to the base of switching transistor 490 through an input network of resistors 492 and 494. A collector resistor 496 is tied to +5 volts, with the Left End signal being obtained at the collector of transistor 490.

A similar arrangement exists for the circuitry to generate the Right End signal. That is, the emitter of the phototransistor in optocoupler 486 is connected to the base lead of transistor 498 through an input network of resistors 500 and 502. A collector resistor 504 is further provided. Since flag 142 on the threaded reciprocating block can be at only end or the other, the Left End and Right End signals produce mutually exclusive (in time occurrence) logic one signals.

Referring to FIGS. 9 and 10 in conjunction, a logic one for the left End signal will send the output of NOR gate 480 low, thereby triggering one-shot 476. The logic zero output of NOR gate 480, which is applied as one input to NOR gate 482, coupled with the logic zero condition of the Right End signal will place the output of NOR gate 482 at a logic one. This produces no effect on one-shot 478, but latches the R-S flip-flop of NOR gates 480 and 481. After the metering pump has reversed and the drive shaft has started movement in the opposite direction, the Left End signal will return to a logic zero. When the drive shaft has traveled all the way to the opposite end, the flag will cause the Right End signal to become a logic one. This will cause the output of NOR gate 482 to assume a logic zero condition, which, of course, triggers one-shot 478.

The direction signal DIR applied to flip-flop 386 in FIG. 8 is generated by D flip-flop 506 in FIG. 9. The output of NOR gate 482 is applied to the D input of flip-flop 506, and clocking of the device is by a clock pulse generated by NOR gate 508. The direction signal DIR is taken from the Q bar output of flip-flop 506. The clock input to flip-flop 506 is obtained from two sources. The first is the Stepper Clk which is delivered by inverter 510 as one input to NOR gate 508. The other signal which can clock flip-flop 506 is the Composite Turnaround signal from circuitry in FIG. 7.

Considering FIGS. 7 and 9 in conjunction, the output of NOR gate 474 is designated as an End Turnaround signal and is applied as the trigger input to one-shot 512 in FIG. 7. The output of the one-shot causes an open collector inverter 514 to pull the base of transistor 220 low through diode 516 and resistor 518. This causes the circuitry that decelerates the motor to go into operation. The output of one-shot 512 returns to FIG. 9 as a Composite Turnaround signal applied as the second input to NOR gate 508. Composite Turnaround will occur while there is no Stepper Clk pulses because the Flow Rate Clock from which Stepper Clk is derived goes to zero.

TABLE II

| Circuit Component Values | | |
|---|---|---|
| FIG. 7 | | |
| Amplifier 71 - | | |
| | op-amp 160 | MC3403 |
| | resistor 162 | 12.1K, 1% |
| | capacitor 164 | .01 microfarad |
| | resistor 166 | 10.0K, 1% |
| | resistor 168 | 5.11K, 1% |
| Amplifier 73 - | | |
| | op-amp 172 | MC3403 |
| | resistor 174 | 7.5K, 1% |
| | resistor 176 | 768, 1% |
| | capacitor 178 | .01 microfarad |
| | resistor 170 | 20K, 1% |
| | resistor 180 | 5.62K, 1% |
| | potentiometer 182 | 10K |
| Cell Excitation Oscillator 86 - | | |
| | timer circuit 230 | NE556 |
| | resistor 232 | 510 |
| | resistor 234 | 2.2K |
| | capacitor 236 | .01 microfarad |
| | capacitor 238 | 1 microfarad, 25V |
| | op-amp 240 | HA-2625-5 |
| | resistor 242 | 5.1K |
| | resistor 244 | 20K |
| | resistor 246 | 100 |
| Pulse Generator 74 - | | |
| | resistor 192,198 | 51K |
| | capacitor 194 | .47 microfarad |

TABLE II-continued

| Circuit Component Values | | |
|---|---|---|
| | op-amp 186 | MC3403 |
| | resistor 188 | 10K |
| | potentiometer 190 | 50K |
| | resistor 198 | 51K |
| | resistor 200 | 100K |
| | capacitor 202 | .01 microfarad |
| | diode 206 | 1N914 |
| | VFC 184 | VFC 32 (Burr-Brown) |
| | resistor 204 | 3.3M |
| | capacitor 185 | 1000 pf |
| | capacitor 187 | 82 pf |
| | resistor 212 | 1K |
| | inverters 208, 210 | SN7414 |
| Electrical Control Circuit 90 - | | |
| | capacitors 250, 252 | 100 microfarad |
| | resistors 256 | 1.00K |
| | diodes 258, 260 268, 292, 516 | 1N914 |
| | op-amp 254 | LH0022 |
| | resistor 262 | 100K, 1% |
| | capacitor 264 | 30 pf |
| | potentiometer 266 | 10K |
| | capacitor 270 | 10 microfarad |
| | resistor 274, 278, 294, 224 | 10K |
| | potentiometer 276 | 2K |
| | resistor 280 | 13K |
| | resistor 288, 518 | 1K |
| | op-amp 284, 272 | MC3403 |
| | capacitor 290 | .001 microfarad |
| | transistor 220 | 2N4403 |
| | resistor 222 | 200 |
| | opto-coupler 214 | H11F3 |
| | resistor 226 | 56K |
| | inverter 514 | SN7414 |
| | timer circuit 512 | NE556 |
| | capacitor 511 | .01 microfarad |
| | resistor 513, 282, 286 | 1M |
| | capacitor 515 | .05 microfarad |
| FIG. 8 | | |
| Winding Drive Circuit 302 - | | |
| | transistors 306, 308 | MJ2500 |
| | 310, 312 | MJ3000 |
| | 371, 372 | 2N3904 |
| | diode bridge 314 | MDA970-1 |
| | resistors 340, 341 | 10K |
| | 338, 339 | 2.7K |
| | 380, 381 | 5.6K |
| | 378, 379 | 1K |
| | 376, 377 | 10K |
| | 374, 375 | 5.1K |
| | capacitors 383, 385 | .01 microfarad |
| | comparators 326, 346 | LM311 |
| | resistors 319, 320, 321, 322 327, 328, 369, 370 329, 330, | .2 (3 watt) |
| | | 1K |
| | 333, 334 | 10K |
| | capacitors 331, 332 | .1 microfarad |
| | inverters 366, 384 | SN7438 |
| Sequence Control Logic - | | |
| | counter 350 | SN74193 |
| | decoder 352 | SN7442 |
| | NAND gates 356, 358, 360, 362, 388, 390 | SN7410 |
| | NAND gates 364, 382 | SN7438 |
| | flip-flop 386 | SN7474 |
| Current Reference Source - | | |
| | transistor 396 | 2N4403 |
| | resistors 404, 392 | 1K |
| | 402 | 10K |
| | 398 | 2K |

TABLE II-continued

| Circuit Component Values | | |
|---|---|---|
| | potentiometer 394 | 500 |
| Timing Circuit - | | |
| | one-shot 408 | MC14528 |
| | transistor 410 | MPSA14 |
| | resistors 412 | 1K |
| | 414, 416 | 10K |
| FIG. 9 | | |
| Stepper Motor Logic - | | |
| | quad D flip-flop 430, 432 | SN74175 |
| | rate multiplier 434, 436 | SN74167 |
| | decade counters 440, 442 | SN7490 |
| | one-shot 446, 476, 478 | SN74123 |
| | resistor 448 | 10K |
| | capacitor 450 | .01 microfarad |
| | gates 452, 464, 474 | SN7400 |
| | counters 458, 460 | SN74193 |
| | D flip-flop 462, 506 | SN7474 |
| | inverters 470, 510 | SN7416 |
| | NOR gates 480, 482, 508 | SN7402 |
| FIG. 10 | | |
| Optical Sensors - | | |
| | resistors 488 | 200 |
| | 492, 500 | 10K |
| | 494, 502 | 100K |
| | 496, 504 | 10K |
| | transistors 490, 498 | 2N3904 |
| | opto-couplers 484, 486 | H13A1 |

*(resistors are in ohms)

The foregoing description of the invention has been directed to a particular preferred embodiment in accordance with the requirements of the Patent Statute and for purposes of explanation and illustration. It will be apparent, however, to those skilled in this art that many modifications and changes may be made without departing from the scope and spirit of the invention. It is the Applicants' intention in the following claims to cover all equivalent implementations, as well as modifications and variations to the preferred embodiment, as fall within the scope of the invention.

What is claimed is:

1. In a liquid chromatograph having solvent mixing apparatus producing a solvent mixture, a controller operative to regulate the total flow rate of the solvent mixture produced by the solvent mixing apparatus, a column, and a solvent mixture flow path defined between the solvent mixing apparatus and the column, the improvement comprising:

a sensing detector cell disposed in the solvent mixture flow path between the solvent mixing apparatus and the column;

the cell having an inlet port for receiving an input flow of solvent mixture into the cell from the solvent mixing apparatus, an outlet port for withdrawal of an output flow of solvent mixture for introduction to the column, and a reservoir between the inlet and outlet ports for holding a volume of solvent mixture accumulated in an amount dependent upon the relative flow rates of the cell input flow and the cell output flow;

the cell having first and second spaced-apart electrodes, one of the electrodes being provided to receive an applied electrical excitation and the other electrode being provided to sense the applied excitation through an accumulated volume of solvent mixture between the electrodes and produce an excitation response signal functionally related to the volume of the accumulated solvent mixture; and an electrical control circuit responsive to the sensing detector cell excitation response signal and coupled to the solvent mixture flow rate controller for effecting a reduction in the total flow rate of the produced solvent mixture when the volume of the accumulated solvent mixture in the cell exceeds a preset amount and for effecting an increase in the total flow rate of the produced solvent mixture when the volume of the solvent mixture accumulated in the cell becomes less than the preset amount.

2. The improvement of claim 1 wherein the sensing detector cell is an electrical admittance measurement cell.

3. In a liquid chromatograph including at least first and second solvent sources, a controller for establishing the composition and total flow rate of a solvent mixture produced, and a column, the improvement comprising:

a first low pressure metering pump for providing a flow of the first solvent;

a second low pressure metering pump for providing a flow of the second solvent;

each pump providing the flow of the respective solvent at a rate dependent upon pump speed as established by the controller;

means receiving the first and second solvent flows for mixing the same at low pressure to produce a solvent mixture flowing at a rate approximately equal to the sum of the individual solvent flow rates;

a high pressure pump taking in solvent mixture at an intake flow rate for driving the column to establish therein a flow of solvent mixture;

a solvent mixture flow path defined between the individual solvent mixing means and the high pressure pump;

a detector cell disposed in the solvent mixture flow path;

the cell having an inlet port for receiving an input flow of solvent mixture into the cell from the solvent mixing means, an outlet port for withdrawal of an output flow of solvent mixture by the high pressure pump, and a reservoir between the inlet and outlet ports for holding a volume of solvent mixture accumulated in an amount dependent upon the relative flow rates of the cell input and output flows;

the cell having first and second spaced-apart electrodes in contact with the solvent mixture accumulated in the cell, one of the electrodes being provided to receive an applied electrical excitation and the other electrode being provided to sense the applied excitation through the accumulated solvent mixture and produce an excitation response functionally related to the volume of the accumulated solvent mixture; and an electrical control circuit connected to the detector cell and coupled to the pump speed controller, the circuit responding to the detector excitation response, to produce a control input to the pump controller for selectively inhibiting and enabling operation of the solvent metering pumps.

4. In a liquid chromatograph having solvent mixing apparatus including two or more solvent metering pumps, each providing a flow of solvent at a rate dependent upon the respective pump speed for combination into a combined solvent flow to form a proportioned solvent mixture at a total flow rate that is the combination of the individual solvent flow rates, and a controller for regulating the total flow rate of the formed solvent mixture by synchronously varying in identical proportion the speeds of the solvent metering pumps, the improvement comprising:

a detector cell having an inlet supply port for receiving the formed solvent mixture at a first flow rate approximating the total flow rate and having an outlet port to provide for withdrawal of the formed solvent mixture from the cell at a second flow rate, the cell holding a volume of solvent mixture accumulated in an amount dependent upon the relative rates at which solvent mixture is received and withdrawn;

the detector cell includes first and second spaced-apart electrodes in contact with the solvent mixture accumulated in the cell, one of the electrodes receiving an applied electrical excitation and the other electrode sensing the applied excitation through the accumulated solvent mixture between the electrodes to produce an excitation response signal functionally related to the volume of the accumulated solvent mixture;

the detector cell being sensitive to the electrical properties of the solvent mixture accumulated in the cell to produce the excitation response signal;

a reference signal source providing a signal representative of a reference volume amount of cell accumulated solvent mixture;

a comparator receiving the detector cell output signal and the reference signal for producing an output signal indicative of the volume amount of accumulated solvent mixture in the detector cell relative to the reference volume amount; and means electrically connected to the comparator and coupled to the pump speed controller for producing a control input to the pump speed controller;

said means producing a control input to the pump speed controller that inhibits operation of the solvent metering pumps in response to a comparator output signal indication that the volume amount of accumulated solvent mixture in the cell is greater than the reference volume amount, and producing a control input to the pump speed controller that enables normal operation of the solvent metering pumps in response to a comparator output signal indication that the volume amount of accumulated solvent mixture in the cell is less than the reference volume amount.

5. In a liquid chromatograph having solvent mixing apparatus producing a solvent mixture flow and including two or more solvent metering pumps, each driven by a stepping motor in response to pulses produced by a pulse generator, the improvement comprising:

a cell for receiving the solvent mixture flow produced by the solvent mixing apparatus and providing for withdrawal therefrom of a solvent mixture flow, the cell holding a volume of solvent mixture accumulated in an amount dependent upon the rates at which solvent mixtures are received and withdrawn;

the cell comprising a chamber having an inlet supply port receiving an input flow of solvent mixture at a first flow rate from the solvent mixing apparatus and an outlet port for withdrawal of an output flow rate at a second flow rate;

a detector sensitive to the volume amount of solvent mixture accumulated in the cell and producing an output signal representative thereof;

the detector comprising an electrical admittance measurement device including first and second spaced-apart electrodes in contact with the solvent mixture accumulating in the cell, one of the electrodes receiving an applied electrical excitation and the other electrode sensing the applied excitation through the accumulated solvent mixture between the electrodes to produce an excitation response output signal functionally related to the volume of the accumulated solvent mixture;

a comparator receiving the detector output signal and a signal representative of a reference volume amount of cell accumulated solvent mixture for comparison;

the comparator producing an output signal of a first signal level when the comparison indicates that the volume amount of solvent mixture in the cell exceeds the reference volume amount and producing an output signal of a second signal level when the comparison indicates that the volume amount of solvent mixture in the cell is less than the reference volume amount;

an electrical output circuit electrically connected to the comparator and coupled to the pulse generator; and the circuit being operable in response to the first signal level of the comparator output signal to inhibit pulse production by the pulse generator and thereby synchronously stop the solvent metering pumps, and the circuit being operable in response to the second signal level of the comparator output signal to enable pulse production by the pulse generator.

* * * * *

UNITED STATES PATENT OFFICE
CERTIFICATE OF CORRECTION

Patent No. 4,311,586   Dated January 19, 1982

Inventor(s) Lawrence G. Baldwin, et al

It is certified that error appears in the above-identified patent and that said Letters Patent are hereby corrected as shown below:

Column 13, line 65, "30" should read -- + --.

Column 14, line 11, "30" should read -- + --.

Column 20, line 9, "selectled" should read -- selected --.

Column 22, line 24, "Q" should read -- $\overline{Q}$ --.

Column 5, line 2, "chormatograph" should read
  -- chromatograph --.

Column 9, line 39, "combing" should read -- combining --.

Column 9, line 54, "wihtin" should read -- within --.

Column 10, line 7, "vlaves" should read -- valves --.

Column 12, line 27, "electircal" should read -- electrical --.

Column 20, line 40, "in" should read -- is --.

Signed and Sealed this

Twentieth Day of April 1982

[SEAL]

Attest:

GERALD J. MOSSINGHOFF

Attesting Officer    Commissioner of Patents and Trademarks